United States Patent
Pulé et al.

(10) Patent No.: US 12,304,942 B2
(45) Date of Patent: May 20, 2025

(54) CELL COMPRISING A CHIMERIC ANTIGEN RECEPTOR OR A TRANSGENIC T-CELL RECEPTOR AND COMPRISING A CHIMERIC TNF RECEPTOR

(71) Applicant: AUTOLUS LIMITED, London (GB)

(72) Inventors: Martin Pulé, London (GB); Marco Della Peruta, London (GB)

(73) Assignee: AUTOLUS LIMITED, London (GB)

( * ) Notice: Subject to any disclaimer, the term of this patent is extended or adjusted under 35 U.S.C. 154(b) by 1190 days.

(21) Appl. No.: 16/772,260

(22) PCT Filed: Dec. 14, 2018

(86) PCT No.: PCT/GB2018/053629
§ 371 (c)(1),
(2) Date: Jun. 12, 2020

(87) PCT Pub. No.: WO2019/116046
PCT Pub. Date: Jun. 20, 2019

(65) Prior Publication Data
US 2021/0095003 A1    Apr. 1, 2021

(30) Foreign Application Priority Data
Dec. 15, 2017   (GB) ..................................... 1720949

(51) Int. Cl.
| | | |
|---|---|---|
| C07K 14/705 | (2006.01) | |
| A61K 40/11 | (2025.01) | |
| A61K 40/31 | (2025.01) | |
| A61K 40/42 | (2025.01) | |
| C07K 14/725 | (2006.01) | |
| C07K 16/30 | (2006.01) | |
| C07K 19/00 | (2006.01) | |
| C12N 5/00 | (2006.01) | |
| C12N 5/0783 | (2010.01) | |
| C07K 16/28 | (2006.01) | |

(52) U.S. Cl.
CPC ........ *C07K 14/70578* (2013.01); *A61K 40/11* (2025.01); *A61K 40/31* (2025.01); *A61K 40/4204* (2025.01); *A61K 40/4211* (2025.01); *A61K 40/4215* (2025.01); *A61K 40/4258* (2025.01); *C07K 14/7051* (2013.01); *C07K 16/30* (2013.01); *C07K 19/00* (2013.01); *C12N 5/0636* (2013.01); *C07K 16/2803* (2013.01); *C07K 2319/02* (2013.01); *C07K 2319/32* (2013.01)

(58) Field of Classification Search
CPC .............. C07K 14/70578; C07K 19/00; C07K 2319/32; C07K 14/7051; C12N 5/0636
See application file for complete search history.

(56) References Cited

U.S. PATENT DOCUMENTS

| | | |
|---|---|---|
| 7,052,906 B1 | 5/2006 | Lawson et al. |
| 2006/0009450 A1 | 1/2006 | Tobinick |
| 2013/0266551 A1 | 10/2013 | Campana et al. |
| 2016/0096892 A1* | 4/2016 | Brogdon ................. A61P 35/00 435/328 |
| 2022/0145325 A1 | 5/2022 | Puléet al. |
| 2022/0364116 A1 | 11/2022 | Puléet al. |
| 2023/0113183 A1 | 4/2023 | McKenzie et al. |

FOREIGN PATENT DOCUMENTS

| | | |
|---|---|---|
| WO | WO-02/36769 A2 | 5/2002 |
| WO | WO-2005/044996 A2 | 5/2005 |
| WO | WO-2013/033626 A2 | 3/2013 |
| WO | WO-2013/153391 A1 | 10/2013 |
| WO | WO-2016/014576 A1 | 1/2016 |
| WO | WO-2016/093878 A1 | 6/2016 |
| WO | WO-2016/174461 A1 | 11/2016 |
| WO | WO-2017/028374 A1 | 2/2017 |
| WO | WO-2020/183131 A1 | 9/2020 |
| WO | WO-2021/205176 A2 | 10/2021 |

OTHER PUBLICATIONS

Wang et al, 2012. Immunology. 137: 114-116.*
Tokuriki et al, 2009, Current Opinion in Structural Biology. 19: 596-604.*
Bhattacharya et al, 2017. Plos One. 12(3): e0171355, pp. 1-22 as printed.*
Donnelly et al., "The 'cleavage' activities of foot-and-mouth disease virus 2A site-directed mutants and naturally occurring '2A-like' sequences," J. Gen. Virol. 82:1027-1041 (2001).
International Search Report and Written Opinion from International Application No. PCT/GB2018/053629 dated Feb. 19, 2019.
Wang et al., "Preclinical Evaluation of Chimeric Antigen Receptors Targeting CD70-Expressing Cancers," Clinical Cancer Research 23(9):2267-2276 (2017).
Watts, "TNF/TNFR Family Members in Costimulation of T Cell Responses," Annu. Rev. Immunol. 23:23-68 (2005).
Long et al., "4-1BB Costimulation Ameliorates T Cell Exhaustion Induced by Tonic Signaling of Chimeric Antigen Receptors," Nature Medicine, 21(6):581-590 (2015).
Van der Stegen et al., "The Pharmacology of Second-Generation Chimeric Antigen Receptors," Nature Reviews Drug Discovery, 15(7):499-509 (2015).
McKenzie C., et al., "Novel Fas-TNFR Chimeras that Prevent Fas Ligand-Mediated Kill and Signal Synergistically to Enhance CART Cell Efficacy", Molecular Therapy-Nucleic Acids, vol. 32, XP093069478, Jun. 1, 2023, pp. 603-621.
Oda S.K., et al., "A Fas-4-1BB Fusion Protein Converts a Death to a Pro-Survival Signal and Enhances T Cell Therapy", Journal of Experimental Medicine, XP55842282A, vol. 217, No. 12, 2020, 20 Pages.

* cited by examiner

*Primary Examiner* — Zachary C Howard
(74) *Attorney, Agent, or Firm* — MARSHALL, GERSTEIN & BORUN LLP

(57) ABSTRACT

The present invention relates to a cell which comprises; (i) a chimeric antigen receptor (CAR) or a transgenic T-cell receptor (TCR); and (ii) a chimeric TNF receptor (TNFR) which comprises (a) a binding domain which is capable of binding a TNFR ligand; and (b) a TNFR signalling domain.

3 Claims, 5 Drawing Sheets

Specification includes a Sequence Listing.

SEQUENCE LISTING

<160> NUMBER OF SEQ ID NOS: 37

<210> SEQ ID NO 1
<211> LENGTH: 268
<212> TYPE: PRT
<213> ORGANISM: Artificial Sequence
<220> FEATURE:
<223> OTHER INFORMATION: D3R/4-1BB chimeric TNFR

<400> SEQUENCE: 1

Met Glu Gln Arg Pro Arg Gly Cys Ala Ala Val Ala Ala Ala Leu Leu
1               5                   10                  15

Leu Val Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
                35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
                100                 105                 110

Thr Arg Cys Gly Cys Lys Pro Gly Trp Phe Val Glu Cys Gln Val Ser
            115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
            165                 170                 175

Val Ser Cys Pro Thr Ser Thr Leu Gly Ser Cys Pro Glu Arg Cys Ala
            180                 185                 190

Ala Val Cys Gly Trp Arg Gln Ile Ile Ser Phe Phe Leu Ala Leu Thr
            195                 200                 205

Ser Thr Ala Leu Leu Phe Leu Phe Leu Thr Leu Arg Phe Ser
    210                 215                 220

Val Val Lys Arg Gly Arg Lys Lys Leu Leu Tyr Ile Phe Lys Gln Pro
225                 230                 235                 240

Phe Met Arg Pro Val Gln Thr Thr Gln Glu Glu Asp Gly Cys Ser Cys
                245                 250                 255

Arg Phe Pro Glu Glu Glu Gly Gly Cys Glu Leu
            260                 265

<210> SEQ ID NO 2
<211> LENGTH: 271
<212> TYPE: PRT
<213> ORGANISM: Artificial Sequence
<220> FEATURE:
<223> OTHER INFORMATION: HVEM/4-1BB chimeric TNFR (TNF receptor)

<400> SEQUENCE: 2

Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
    115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Ile Ile Ser Phe Phe Leu
        195                 200                 205

Ala Leu Thr Ser Thr Ala Leu Leu Phe Leu Leu Phe Phe Leu Thr Leu
    210                 215                 220

Arg Phe Ser Val Val Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
                245                 250                 255

Cys Ser Cys Arg Phe Pro Glu Glu Glu Glu Gly Gly Cys Glu Leu
            260                 265                 270

<210> SEQ ID NO 3
<211> LENGTH: 260
<212> TYPE: PRT
<213> ORGANISM: Artificial Sequence
<220> FEATURE:
<223> OTHER INFORMATION: CD27/4-1BB chimeric TNFR

<400> SEQUENCE: 3

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Ile Ser Phe Phe Leu Ala Leu Thr Ser Thr Ala Leu Leu Phe Leu Leu
        195                 200                 205

-continued

```
Phe Phe Leu Thr Leu Arg Phe Ser Val Val Lys Arg Gly Lys Lys
        210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu
            260

<210> SEQ ID NO 4
<211> LENGTH: 281
<212> TYPE: PRT
<213> ORGANISM: Artificial Sequence
<220> FEATURE:
<223> OTHER INFORMATION: RANK/4-1BB chimeric TNFR

<400> SEQUENCE: 4

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
                20                  25                  30

Pro Cys Thr Ser Glu Lys His Tyr Glu His Leu Gly Arg Cys Cys Asn
            35                  40                  45

Lys Cys Glu Pro Gly Lys Tyr Met Ser Ser Lys Cys Thr Thr Thr Ser
50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
                100                 105                 110

Ala Cys Thr Ala Gly Tyr His Trp Ser Gln Asp Cys Glu Cys Cys Arg
            115                 120                 125

Arg Asn Thr Glu Cys Ala Pro Gly Leu Gly Ala Gln His Pro Leu Gln
130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Ile Ile Ser Phe Phe Leu Ala Leu Thr Ser Thr Ala
    210                 215                 220

Leu Leu Phe Leu Leu Phe Phe Leu Thr Leu Arg Phe Ser Val Val Lys
225                 230                 235                 240

Arg Gly Arg Lys Lys Leu Leu Tyr Ile Phe Lys Gln Pro Phe Met Arg
                245                 250                 255

Pro Val Gln Thr Thr Gln Glu Glu Asp Gly Cys Ser Cys Arg Phe Pro
            260                 265                 270

Glu Glu Glu Glu Gly Gly Cys Glu Leu
            275                 280

<210> SEQ ID NO 5
```

```
<211> LENGTH: 151
<212> TYPE: PRT
<213> ORGANISM: Artificial Sequence
<220> FEATURE:
<223> OTHER INFORMATION: Fn14/4-1BB chimeric TNFR

<400> SEQUENCE: 5

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Asp Trp Cys Ser Arg Gly Ser Ser Trp Ser Ala Asp Leu
            35                  40                  45

Asp Lys Cys Met Asp Cys Ala Ser Cys Arg Ala Arg Pro His Ser Asp
        50                  55                  60

Phe Cys Leu Gly Cys Ala Ala Pro Ala Pro Phe Arg Leu Leu
65                  70                  75                  80

Trp Pro Ile Ile Ser Phe Phe Leu Ala Leu Thr Ser Thr Ala Leu Leu
                85                  90                  95

Phe Leu Leu Phe Phe Leu Thr Leu Arg Phe Ser Val Val Lys Arg Gly
                100                 105                 110

Arg Lys Lys Leu Leu Tyr Ile Phe Lys Gln Pro Phe Met Arg Pro Val
            115                 120                 125

Gln Thr Thr Gln Glu Glu Asp Gly Cys Ser Cys Arg Phe Pro Glu Glu
        130                 135                 140

Glu Glu Gly Gly Cys Glu Leu
145                 150

<210> SEQ ID NO 6
<211> LENGTH: 409
<212> TYPE: PRT
<213> ORGANISM: Artificial Sequence
<220> FEATURE:
<223> OTHER INFORMATION: CD27/DR3 chimeric TNFR

<400> SEQUENCE: 6

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
```

```
                    165                 170                 175
His Trp Pro Pro Gln Arg Ser Leu Cys Ser Ser Asp Phe Ile Arg Met
            180                 185                 190
Phe Trp Val Gln Val Leu Leu Ala Gly Leu Val Val Pro Leu Leu Leu
                195                 200                 205
Gly Ala Thr Leu Thr Tyr Thr Tyr Arg His Cys Trp Pro His Lys Pro
            210                 215                 220
Leu Val Thr Ala Asp Glu Ala Gly Met Glu Ala Leu Thr Pro Pro Pro
225                 230                 235                 240
Ala Thr His Leu Ser Pro Leu Asp Ser Ala His Thr Leu Leu Ala Pro
                245                 250                 255
Pro Asp Ser Ser Glu Lys Ile Cys Thr Val Gln Leu Val Gly Asn Ser
            260                 265                 270
Trp Thr Pro Gly Tyr Pro Glu Thr Gln Glu Ala Leu Cys Pro Gln Val
            275                 280                 285
Thr Trp Ser Trp Asp Gln Leu Pro Ser Arg Ala Leu Gly Pro Ala Ala
            290                 295                 300
Ala Pro Thr Leu Ser Pro Glu Ser Pro Ala Gly Ser Pro Ala Met Met
305                 310                 315                 320
Leu Gln Pro Gly Pro Gln Leu Tyr Asp Val Met Asp Ala Val Pro Ala
                325                 330                 335
Arg Arg Trp Lys Glu Phe Val Arg Thr Leu Gly Leu Arg Glu Ala Glu
            340                 345                 350
Ile Glu Ala Val Glu Val Glu Ile Gly Arg Phe Arg Asp Gln Gln Tyr
                355                 360                 365
Glu Met Leu Lys Arg Trp Arg Gln Gln Gln Pro Ala Gly Leu Gly Ala
            370                 375                 380
Val Tyr Ala Ala Leu Glu Arg Met Gly Leu Asp Gly Cys Val Glu Asp
385                 390                 395                 400
Leu Arg Ser Arg Leu Gln Arg Gly Pro
                405

<210> SEQ ID NO 7
<211> LENGTH: 191
<212> TYPE: PRT
<213> ORGANISM: Artificial Sequence
<220> FEATURE:
<223> OTHER INFORMATION: ligand binding domain of CD27

<400> SEQUENCE: 7

Met Ala Arg Pro His Pro Trp Trp Leu Cys Val Leu Gly Thr Leu Val
1               5                   10                  15
Gly Leu Ser Ala Thr Pro Ala Pro Lys Ser Cys Pro Glu Arg His Tyr
                20                  25                  30
Trp Ala Gln Gly Lys Leu Cys Cys Gln Met Cys Glu Pro Gly Thr Phe
            35                  40                  45
Leu Val Lys Asp Cys Asp Gln His Arg Lys Ala Ala Gln Cys Asp Pro
        50                  55                  60
Cys Ile Pro Gly Val Ser Phe Ser Pro Asp His His Thr Arg Pro His
65                  70                  75                  80
Cys Glu Ser Cys Arg His Cys Asn Ser Gly Leu Leu Val Arg Asn Cys
                85                  90                  95
Thr Ile Thr Ala Asn Ala Glu Cys Ala Cys Arg Asn Gly Trp Gln Cys
                100                 105                 110
Arg Asp Lys Glu Cys Thr Glu Cys Asp Pro Leu Pro Asn Pro Ser Leu
```

```
                   115                 120                 125

Thr Ala Arg Ser Ser Gln Ala Leu Ser Pro His Pro Gln Pro Thr His
            130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                    165                 170                 175

His Trp Pro Pro Gln Arg Ser Leu Cys Ser Ser Asp Phe Ile Arg
                180                 185                 190

<210> SEQ ID NO 8
<211> LENGTH: 212
<212> TYPE: PRT
<213> ORGANISM: Artificial Sequence
<220> FEATURE:
<223> OTHER INFORMATION: ligand binding domain of RANK

<400> SEQUENCE: 8

Met Ala Pro Arg Ala Arg Arg Arg Pro Leu Phe Ala Leu Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro
    210

<210> SEQ ID NO 9
<211> LENGTH: 82
<212> TYPE: PRT
<213> ORGANISM: Artificial Sequence
<220> FEATURE:
<223> OTHER INFORMATION: ligand binding domain of Fn14

<400> SEQUENCE: 9

Met Ala Arg Gly Ser Leu Arg Arg Leu Leu Arg Leu Leu Val Leu Gly
1               5                   10                  15
```

```
Leu Trp Leu Ala Leu Leu Arg Ser Val Ala Gly Glu Gln Ala Pro Gly
                20                  25                  30

Thr Ala Pro Asp Trp Cys Ser Arg Gly Ser Ser Trp Ser Ala Asp Leu
            35                  40                  45

Asp Lys Cys Met Asp Cys Ala Ser Cys Arg Ala Arg Pro His Ser Asp
 50                  55                  60

Phe Cys Leu Gly Cys Ala Ala Pro Pro Ala Pro Phe Arg Leu Leu
 65                  70                  75                  80

Trp Pro
```

<210> SEQ ID NO 10
<211> LENGTH: 202
<212> TYPE: PRT
<213> ORGANISM: Artificial Sequence
<220> FEATURE:
<223> OTHER INFORMATION: ligand binding domain of HVEM

<400> SEQUENCE: 10

```
Met Glu Pro Pro Gly Asp Trp Gly Pro Pro Trp Arg Ser Thr Pro
 1               5                  10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
 50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val
            195                 200
```

<210> SEQ ID NO 11
<211> LENGTH: 199
<212> TYPE: PRT
<213> ORGANISM: Artificial Sequence
<220> FEATURE:
<223> OTHER INFORMATION: ligand binding domain of DR3

<400> SEQUENCE: 11

```
Met Glu Gln Arg Pro Arg Gly Cys Ala Ala Val Ala Ala Ala Leu Leu
 1               5                  10                  15

Leu Val Leu Leu Gly Ala Arg Ala Gln Gly Gly Thr Arg Ser Pro Arg
                20                  25                  30
```

```
Cys Asp Cys Ala Gly Asp Phe His Lys Lys Ile Gly Leu Phe Cys Cys
             35                  40                  45
Arg Gly Cys Pro Ala Gly His Tyr Leu Lys Ala Pro Cys Thr Glu Pro
 50                  55                  60
Cys Gly Asn Ser Thr Cys Leu Val Cys Pro Gln Asp Thr Phe Leu Ala
 65                  70                  75                  80
Trp Glu Asn His His Asn Ser Glu Cys Ala Arg Cys Gln Ala Cys Asp
                 85                  90                  95
Glu Gln Ala Ser Gln Val Ala Leu Glu Asn Cys Ser Ala Val Ala Asp
            100                 105                 110
Thr Arg Cys Gly Cys Lys Pro Gly Trp Phe Val Glu Cys Gln Val Ser
            115                 120                 125
Gln Cys Val Ser Ser Ser Pro Phe Tyr Cys Gln Pro Cys Leu Asp Cys
            130                 135                 140
Gly Ala Leu His Arg His Thr Arg Leu Leu Cys Ser Arg Arg Asp Thr
145                 150                 155                 160
Asp Cys Gly Thr Cys Leu Pro Gly Phe Tyr Glu His Gly Asp Gly Cys
                165                 170                 175
Val Ser Cys Pro Thr Ser Thr Leu Gly Ser Cys Pro Glu Arg Cys Ala
            180                 185                 190
Ala Val Cys Gly Trp Arg Gln
            195

<210> SEQ ID NO 12
<211> LENGTH: 42
<212> TYPE: PRT
<213> ORGANISM: Artificial Sequence
<220> FEATURE:
<223> OTHER INFORMATION: 4-1BB signalling domain

<400> SEQUENCE: 12

Lys Arg Gly Arg Lys Lys Leu Leu Tyr Ile Phe Lys Gln Pro Phe Met
 1               5                  10                  15
Arg Pro Val Gln Thr Thr Gln Glu Glu Asp Gly Cys Ser Cys Arg Phe
             20                  25                  30
Pro Glu Glu Glu Glu Gly Gly Cys Glu Leu
             35                  40

<210> SEQ ID NO 13
<211> LENGTH: 36
<212> TYPE: PRT
<213> ORGANISM: Artificial Sequence
<220> FEATURE:
<223> OTHER INFORMATION: OX40 signalling domain

<400> SEQUENCE: 13

Arg Asp Gln Arg Leu Pro Pro Asp Ala His Lys Pro Pro Gly Gly Gly
 1               5                  10                  15
Ser Phe Arg Thr Pro Ile Gln Glu Glu Gln Ala Asp Ala His Ser Thr
             20                  25                  30
Leu Ala Lys Ile
         35

<210> SEQ ID NO 14
<211> LENGTH: 58
<212> TYPE: PRT
<213> ORGANISM: Artificial Sequence
<220> FEATURE:
<223> OTHER INFORMATION: GITR signalling domain
```

<400> SEQUENCE: 14

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Arg Gly Glu Arg Ser Ala Glu
        35                  40                  45

Glu Lys Gly Arg Leu Gly Asp Leu Trp Val
    50                  55

<210> SEQ ID NO 15
<211> LENGTH: 48
<212> TYPE: PRT
<213> ORGANISM: Artificial Sequence
<220> FEATURE:
<223> OTHER INFORMATION: CD27 signalling domain

<400> SEQUENCE: 15

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 16
<211> LENGTH: 62
<212> TYPE: PRT
<213> ORGANISM: Artificial Sequence
<220> FEATURE:
<223> OTHER INFORMATION: CD40 signalling domain

<400> SEQUENCE: 16

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 17
<211> LENGTH: 197
<212> TYPE: PRT
<213> ORGANISM: Artificial Sequence
<220> FEATURE:
<223> OTHER INFORMATION: D3R signalling domain

<400> SEQUENCE: 17

Thr Tyr Thr Tyr Arg His Cys Trp Pro His Lys Pro Leu Val Thr Ala
1               5                   10                  15

Asp Glu Ala Gly Met Glu Ala Leu Thr Pro Pro Ala Thr His Leu
            20                  25                  30

Ser Pro Leu Asp Ser Ala His Thr Leu Leu Ala Pro Asp Ser Ser
        35                  40                  45

Glu Lys Ile Cys Thr Val Gln Leu Val Gly Asn Ser Trp Thr Pro Gly
    50                  55                  60

Tyr Pro Glu Thr Gln Glu Ala Leu Cys Pro Gln Val Thr Trp Ser Trp
65                  70                  75                  80

Asp Gln Leu Pro Ser Arg Ala Leu Gly Pro Ala Ala Pro Thr Leu
                85                  90                  95

Ser Pro Glu Ser Pro Ala Gly Ser Pro Ala Met Met Leu Gln Pro Gly
            100                 105                 110

Pro Gln Leu Tyr Asp Val Met Asp Ala Val Pro Ala Arg Arg Trp Lys
        115                 120                 125

Glu Phe Val Arg Thr Leu Gly Leu Arg Glu Ala Glu Ile Glu Ala Val
    130                 135                 140

Glu Val Glu Ile Gly Arg Phe Arg Asp Gln Gln Tyr Glu Met Leu Lys
145                 150                 155                 160

Arg Trp Arg Gln Gln Gln Pro Ala Gly Leu Gly Ala Val Tyr Ala Ala
                165                 170                 175

Leu Glu Arg Met Gly Leu Asp Gly Cys Val Glu Asp Leu Arg Ser Arg
            180                 185                 190

Leu Gln Arg Gly Pro
        195

<210> SEQ ID NO 18
<211> LENGTH: 27
<212> TYPE: PRT
<213> ORGANISM: Artificial Sequence
<220> FEATURE:
<223> OTHER INFORMATION: transmembrane domain sequence

<400> SEQUENCE: 18

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 19
<211> LENGTH: 27
<212> TYPE: PRT
<213> ORGANISM: Artificial Sequence
<220> FEATURE:
<223> OTHER INFORMATION: 4-1BB transmembrane domain

<400> SEQUENCE: 19

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 20
<211> LENGTH: 21
<212> TYPE: PRT
<213> ORGANISM: Artificial Sequence
<220> FEATURE:
<223> OTHER INFORMATION: DR3 transmembrane domain

<400> SEQUENCE: 20

Met Phe Trp Val Gln Val Leu Leu Ala Gly Leu Val Val Pro Leu Leu
1               5                   10                  15

Leu Gly Ala Thr Leu
            20

<210> SEQ ID NO 21
<211> LENGTH: 21
<212> TYPE: PRT
<213> ORGANISM: Artificial Sequence
<220> FEATURE:

-continued

```
<223> OTHER INFORMATION: OX40 transmembrane domain

<400> SEQUENCE: 21

Val Ala Ala Ile Leu Gly Leu Gly Leu Val Leu Gly Leu Leu Gly Pro
1               5                   10                  15

Leu Ala Ile Leu Leu
            20

<210> SEQ ID NO 22
<211> LENGTH: 21
<212> TYPE: PRT
<213> ORGANISM: Artificial Sequence
<220> FEATURE:
<223> OTHER INFORMATION: GITR transmembrane domain

<400> SEQUENCE: 22

Leu Gly Trp Leu Thr Val Val Leu Leu Ala Val Ala Ala Cys Val Leu
1               5                   10                  15

Leu Leu Thr Ser Ala
            20

<210> SEQ ID NO 23
<211> LENGTH: 21
<212> TYPE: PRT
<213> ORGANISM: Artificial Sequence
<220> FEATURE:
<223> OTHER INFORMATION: CD70 transmembrane domain

<400> SEQUENCE: 23

Val Leu Arg Ala Ala Leu Val Pro Leu Val Ala Gly Leu Val Ile Cys
1               5                   10                  15

Leu Val Val Cys Ile
            20

<210> SEQ ID NO 24
<211> LENGTH: 22
<212> TYPE: PRT
<213> ORGANISM: Artificial Sequence
<220> FEATURE:
<223> OTHER INFORMATION: CD40 transmembrane domain

<400> SEQUENCE: 24

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 25
<211> LENGTH: 193
<212> TYPE: PRT
<213> ORGANISM: Artificial Sequence
<220> FEATURE:
<223> OTHER INFORMATION: CD27 sequence

<400> SEQUENCE: 25

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60
```

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 26
<211> LENGTH: 277
<212> TYPE: PRT
<213> ORGANISM: Artificial Sequence
<220> FEATURE:
<223> OTHER INFORMATION: CD40 sequence

<400> SEQUENCE: 26

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
            245                 250                 255

Gly Cys Gln Pro Val Thr Gln Glu Asp Gly Lys Glu Ser Arg Ile Ser
        260                 265                 270

Val Gln Glu Arg Gln
        275

<210> SEQ ID NO 27
<211> LENGTH: 417
<212> TYPE: PRT
<213> ORGANISM: Artificial Sequence
<220> FEATURE:
<223> OTHER INFORMATION: D3R sequence

<400> SEQUENCE: 27

Met Glu Gln Arg Pro Arg Gly Cys Ala Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
            325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 28
<211> LENGTH: 283
<212> TYPE: PRT
<213> ORGANISM: Artificial Sequence
<220> FEATURE:
<223> OTHER INFORMATION: HVEM sequence

<400> SEQUENCE: 28

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu

```
                    245                 250                 255
Ala Leu Gln Ala Pro Asp Val Thr Thr Val Ala Val Glu Glu Thr
            260                 265                 270

Ile Pro Ser Phe Thr Gly Arg Ser Pro Asn His
            275                 280

<210> SEQ ID NO 29
<211> LENGTH: 616
<212> TYPE: PRT
<213> ORGANISM: Artificial Sequence
<220> FEATURE:
<223> OTHER INFORMATION: RANK sequence

<400> SEQUENCE: 29

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala
                20                  25                  30

Pro Pro Cys Thr Ser Glu Lys His Tyr Glu His Leu Gly Arg Cys Cys Asn
            35                  40                  45

Lys Cys Glu Pro Gly Lys Tyr Met Ser Ser Lys Cys Thr Thr Thr Ser
50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
            115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
            195                 200                 205

Val Tyr Leu Pro Gly Leu Ile Ile Leu Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
            275                 280                 285

Thr Leu Glu Glu Lys Thr Phe Pro Glu Asp Met Cys Tyr Pro Asp Gln
    290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
```

```
                    325                 330                 335
Glu Asp Ser Phe Arg Gln Met Pro Thr Glu Asp Glu Tyr Met Asp Arg
                340                 345                 350

Pro Ser Gln Pro Thr Asp Gln Leu Leu Phe Leu Thr Glu Pro Gly Ser
            355                 360                 365

Lys Ser Thr Pro Pro Phe Ser Glu Pro Leu Glu Val Gly Glu Asn Asp
        370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
                420                 425                 430

His Trp Ala Ala Ser Pro Ser Pro Asn Trp Ala Asp Val Cys Thr Gly
            435                 440                 445

Cys Arg Asn Pro Pro Gly Glu Asp Cys Glu Pro Leu Val Gly Ser Pro
        450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
        530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

<210> SEQ ID NO 30
<211> LENGTH: 129
<212> TYPE: PRT
<213> ORGANISM: Artificial Sequence
<220> FEATURE:
<223> OTHER INFORMATION: Fn14 sequence

<400> SEQUENCE: 30

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Pro
```

```
                65               70               75               80
Ile Leu Gly Gly Ala Leu Ser Leu Thr Phe Val Leu Gly Leu Leu Ser
                        85                90                95

Gly Phe Leu Val Trp Arg Arg Cys Arg Arg Arg Glu Lys Phe Thr Thr
                100               105               110

Pro Ile Glu Glu Thr Gly Gly Gly Cys Pro Ala Val Ala Leu Ile
                115               120               125

Gln

<210> SEQ ID NO 31
<211> LENGTH: 112
<212> TYPE: PRT
<213> ORGANISM: Artificial Sequence
<220> FEATURE:
<223> OTHER INFORMATION: CD3-zeta endodomain

<400> SEQUENCE: 31

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 32
<211> LENGTH: 368
<212> TYPE: PRT
<213> ORGANISM: Artificial Sequence
<220> FEATURE:
<223> OTHER INFORMATION: 4-1BB and CD3-zeta endodomains

<400> SEQUENCE: 32

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
```

```
                130             135                 140
Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
    290                 295                 300

Gln Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
                340                 345                 350

Thr Lys Asp Thr Tyr Asp Ala Leu His Met Gln Ala Leu Pro Pro Arg
            355                 360                 365

<210> SEQ ID NO 33
<211> LENGTH: 152
<212> TYPE: PRT
<213> ORGANISM: Artificial Sequence
<220> FEATURE:
<223> OTHER INFORMATION: CD28 and CD3-zeta endodomains

<400> SEQUENCE: 33

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
                20                  25                  30

Arg Asp Phe Ala Ala Tyr Arg Ser Arg Val Lys Phe Ser Arg Ser Ala
            35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
        115                 120                 125

Leu Tyr Gln Gly Leu Ser Thr Ala Thr Lys Asp Thr Tyr Asp Ala Leu
```

His Met Gln Ala Leu Pro Pro Arg
145                 150

<210> SEQ ID NO 34
<211> LENGTH: 188
<212> TYPE: PRT
<213> ORGANISM: Artificial Sequence
<220> FEATURE:
<223> OTHER INFORMATION: CD28, OX40 and CD3-zeta endodomains

<400> SEQUENCE: 34

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Gly Ser Phe Arg Thr Pro Ile Gln Glu
    50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
        115                 120                 125

Asn Pro Gln Glu Gly Leu Tyr Asn Glu Leu Gln Lys Asp Lys Met Ala
    130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 35
<211> LENGTH: 4
<212> TYPE: PRT
<213> ORGANISM: Artificial Sequence
<220> FEATURE:
<223> OTHER INFORMATION: ITAM (immunoreceptor tyrosine-based activation
      motif)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be Leu or Ile

<400> SEQUENCE: 35

Tyr Xaa Xaa Xaa
1

<210> SEQ ID NO 36
<211> LENGTH: 4
<212> TYPE: PRT
<213> ORGANISM: Artificial Sequence
<220> FEATURE:

-continued

```
<223> OTHER INFORMATION: basic amino acid furin target sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa may be Arg or Lys

<400> SEQUENCE: 36

Arg Xaa Xaa Arg
1

<210> SEQ ID NO 37
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 37

Glu Asn Leu Tyr Phe Gln Ser
1               5
```

CELL COMPRISING A CHIMERIC ANTIGEN RECEPTOR OR A TRANSGENIC T-CELL RECEPTOR AND COMPRISING A CHIMERIC TNF RECEPTOR

CROSS-REFERENCE TO RELATED APPLICATIONS

This is a U.S. National Phase of International Application No. PCT/GB2018/053629, filed Dec. 14, 2018, which claims priority to Great Britain Application No. 1720949.5, filed Dec. 15, 2017.

FIELD OF THE INVENTION

The present invention relates to an engineered cell which expresses a chimeric antigen receptor (CAR) or a transgenic T-cell receptor (TCR); and in particular to approaches to control the proliferation and survival of such cells.

BACKGROUND TO THE INVENTION

Antigen-specific T-cells may be generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T-cells specific to any surface antigen by ex vivo viral vector transduction of a bulk population of peripheral blood T-cells.

TNF-family co-stimulatory molecules provide survival and expansion signals for T-cells during their ontogeny. These TNF receptors (TNFRs) signal via TNF receptor associated factor (TRAF) second messengers. However, the context of these co-stimulatory signals is critical and distinct: for a T-cell to receive such a signal, both the receptor and ligand must be expressed at the same time and at the same place. For instance, for a T-cell to receive a CD27 signal, it must express the CD27 receptor and the cognate ligand CD70 must either be expressed by the T-cell itself or by other cells it is in contact with. This is very tightly controlled: for instance, 4-1BB/4-1BBL and OX40/OX40L are both expressed during a short period after activation on CD8+ and CD4+ T-cells/antigen presenting cells only if antigen is present.

This orchestration is key to physiological immune response to a viral infection, for example. However, a CAR T-cell response does not typically involve an array of accessory immune cells, but rather the CAR T-cell has to survive in the context of a hostile microenvironment with very little immunological cues. CAR T-cell efficacy depends on proliferation and engraftment of the CAR T-cells.

Accordingly, there remains a need for approaches to improve the effectiveness of engineered cells to proliferate, survive and/or engraft in a microenvironment in which the appropriate immunological cues may not be provided.

SUMMARY OF THE INVENTION

In a first aspect the present invention provides a cell which comprises; (i) a chimeric antigen receptor (CAR) or a transgenic T-cell receptor (TCR); and (ii) a chimeric TNF receptor (TNFR) which comprises (a) a binding domain which is capable of binding a TNFR ligand; and (b) a TNFR signalling domain.

The use of a chimeric TNFR as provided by the present invention enables the tight temporal and/or spatial control of TNFR signalling to be decoupled in order to provide improved survival signals for engineered cells, for example CAR T cells. Accordingly, the chimeric TNFR of the present invention may compensate for the lack of a complete physiological immune response in a tumour microenvironment. By way of example, the chimeric TNFR may be constructed such that the antigen-binding domain is engaged, and thus a required co-stimulatory signal induced, in the expected microenvironment in which activity of the engineered cell is required.

The antigen-binding domain of the chimeric TNFR may comprise the ligand binding domain of a TNFR. For example, the antigen-binding domain may comprise the ligand binding domain of DR3, HVEM, CD27, CD40, RANK or Fn14.

The signalling domain of the chimeric TNFR may be an activating signalling domain. For example, the signalling domain may be capable of signalling via TNFR-associated factors (TRAFs). For example, the activating signalling domain may comprise the signalling portion of the 4-1BB, OX40, or GITR endodomain.

The activating signalling domain may comprise the signalling portion of the 4-1BB endodomain.

The signalling domain may not be capable of signal 1 production in the cell. For example, the signalling domain may not comprise a CD3 endodomain. The signalling domain may not comprise a CD3zeta endodomain.

In one embodiment the chimeric TNFR is selected from DR3-4-1BB (SEQ ID NO: 1), HVEM-4-1BB (SEQ ID NO: 2), CD27-4-1BB (SEQ ID NO: 3), RANK-4-1BB (SEQ ID NO: 4), Fn14-4-1BB (SEQ ID NO: 5) and CD27-DR3 (SEQ ID NO: 6) or a variant with at least 80% sequence identity to any of SEQ ID NO: 1-6.

In a further aspect, the present invention comprises a cell which comprises; (i) a chimeric antigen receptor (CAR) or a transgenic T-cell receptor (TCR); and (ii) an exogenous polynucleotide expressing a TNF receptor (TNFR) which is capable of providing a co-stimulatory to the cell following binding of a ligand to the TNFR ligand binding domain.

The exogenous polynucleotide may express CD27, CD40, DR3, HVEM, RANK or Fn14.

The exogenous polynucleotide may express CD27 or CD40.

The cell may an alpha-beta T cell, a NK cell, a gamma-delta T cell, or a cytokine induced killer cell.

In another aspect the present invention provides a chimeric TNF receptor (TNFR) which comprises (a) a binding domain which is capable of binding a TNFR ligand; and (b) a TNFR signalling domain which is not capable of signal 1 production.

The signalling domain may not comprise a CD3 endodomain. The signalling domain may not comprise a CD3zeta endodomain.

The antigen-binding domain of the chimeric TNFR may not be capable of binding CD70.

In a further aspect the present invention provides a nucleic acid construct which comprises:
(i) a first nucleic acid sequence which encodes i) a chimeric antigen receptor (CAR) or a transgenic T-cell receptor (TCR); and
(ii) a second nucleic acid sequence which encodes a chimeric TNF receptor (TNFR) which comprises (a) a binding domain which is capable of binding a TNFR ligand; and (b) a TNFR signalling domain.

The second nucleic acid sequences may encode any chimeric TNFR as provided by the present invention.

The first and second nucleic acid sequences may be separated by a co-expression site.

The present invention further provides a nucleic acid sequence which encodes a chimeric TNF receptor (TNFR) according to the present invention.

In another aspect the present invention provides a kit of nucleic acid sequences comprising:
(i) a first nucleic acid sequence which encodes i) a chimeric antigen receptor (CAR) or a transgenic T-cell receptor (TCR); and
(ii) a second nucleic acid sequence which encodes a chimeric TNF receptor (TNFR) which comprises (a) a binding domain which is capable of binding a TNFR ligand; and (b) a TNFR signalling domain. The chimeric TNFR may be any chimeric TNFR as provided by the present invention.

The present invention also provides a vector which comprises a nucleic acid construct according to the present invention.

In another aspect the present invention provides a kit of vectors which comprises:
(i) a first vector which comprises a nucleic acid sequence which encodes i) a chimeric antigen receptor (CAR) or a transgenic T-cell receptor (TCR); and
(ii) a second vector which comprises a nucleic acid sequence which encodes a chimeric TNF receptor (TNFR) which comprises (a) a binding domain which is capable of binding a TNFR ligand; and (b) a TNFR signalling domain as defined by the present invention.

In another aspect the present invention provides a pharmaceutical composition which comprises a plurality of cells, a nucleic acid construct, a first nucleic acid sequence and a second nucleic acid sequence; a vector or a first and a second vector according to the present invention.

In a further aspect the present invention provides a pharmaceutical composition according to the invention for use in treating and/or preventing a disease.

In another aspect the present invention relates to a method for treating and/or preventing a disease, which comprises the step of administering a pharmaceutical composition according to the invention to a subject in need thereof.

The method may comprise the following steps:
(i) isolation of a cell containing sample;
(ii) transduction or transfection of the cell with a nucleic acid construct, a vector or a first and a second vector according to the present invention; and
(iii) administering the cells from (ii) to a subject.

The cell may autologous. The cell may be allogenic.

In another aspect the present invention relates to the use of a pharmaceutical composition according to the invention in the manufacture of a medicament for the treatment and/or prevention of a disease.

The disease may be cancer.

In another aspect the present invention relates to a method for making a cell according to the present invention, which comprises the step of introducing: a nucleic acid construct, a first nucleic acid sequence and a second nucleic acid sequence, a vector or a first and a second vector of the present invention into the cell.

The cell may be from a sample isolated from a subject.

DETAILED DESCRIPTION OF THE INVENTION

Chimeric Tnf Receptor (TNFR)

Figure 1:
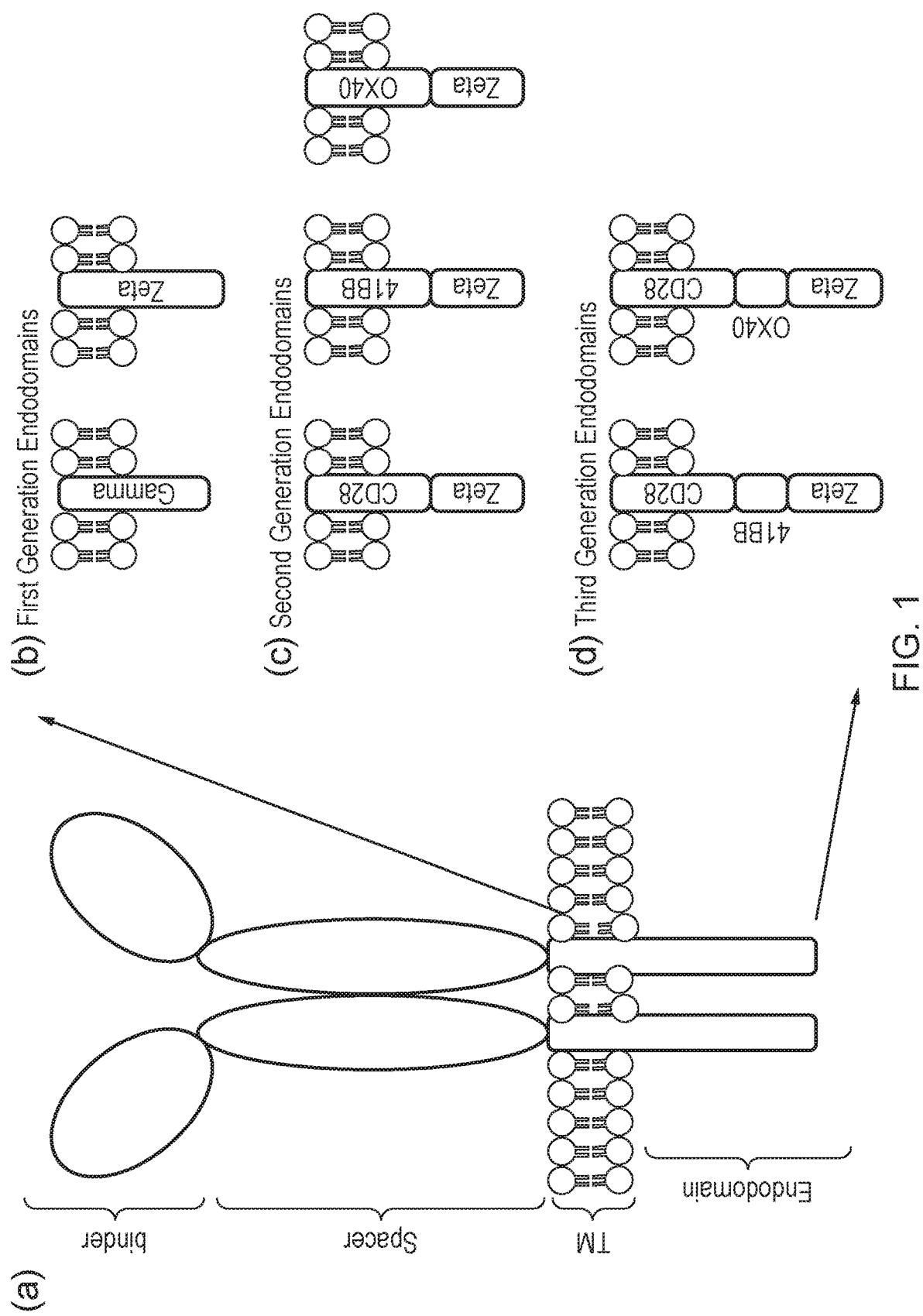
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.
Figure 2:
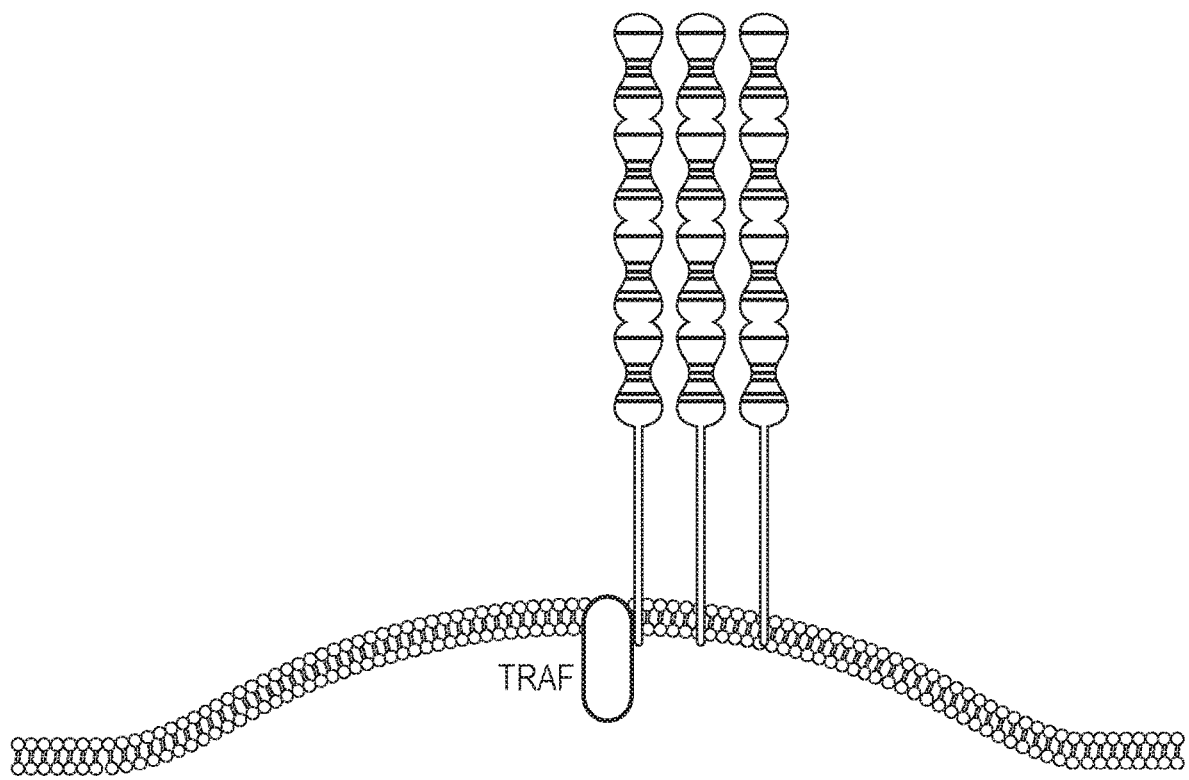
FIG. 2—Schematic diagram illustrating a TNFR

In a first aspect the present invention provides a cell which comprises; (i) a chimeric antigen receptor (CAR) or a transgenic T-cell receptor (TCR); and (ii) a chimeric TNF receptor (TNFR) which comprises (a) a binding domain which is capable of binding a TNFR ligand; and (b) a TNFR signalling domain.

As used herein, a chimeric TNFR refers to a TNFR which comprises (a) a binding domain which is capable of binding a TNFR ligand of a first TNFR; and (b) a TNFR signalling domain of a second TN FR.

Thus, following engagement by a TNFR ligand which typically binds to the first TNFR, the chimeric TNFR of the present invention is capable of transmitting the co-stimulatory signal typically provided by a second TNFR. This enables the tight temporal and/or spatial control of TNFR signalling to be decoupled in order to provide improved survival signals for engineered cells, for example CAR T cells.

By way of example, the chimeric TNFR of the present invention may comprise a binding domain which is capable of binding to a TNFR ligand such as CD70, RANL or TWEAK and the activating signalling domain of a different TNFR such as 41-BB or OX40.

Such chimeric TNFRs may be useful in target certain cancers by coupling the recognition of a TNFR ligand which is abundant in the tumour microenvironment with the co-stimulatory signal of a second TNFR which is typically provided only in a tightly regulated manner. For example, 4-1BB/4-1BBL and OX40/OX40L are both expressed during a short period after activation on CD8+ and CD4+ T-cells/antigen presenting cells only if antigen is present. By way of example, in lymphomas CD70 is abundant so a CD27-4-1BB chimera might be expressed; in lytic bone metastasis RANKL is abundant to RANK-4-1BB might be expressed. In solid cancers, TWEAK is abundant so Fn14-4-1BB might be expressed.

Without wishing to be bound by theory, engineered cells which express a chimeric TNFR that transmits survival and/or proliferative signals in response to the presence of a ligand which is present in a tumour microenvironment will have improved engraftment and expansion compared to corresponding engineered cells without the chimeric TNFR.

TNF Receptors

Members of the TNF receptor superfamily (TNFRSF) are typically Type I transmembrane glycoproteins (N-terminus exterior to the cell). The structural motifs in the cytoplasmic domains of TNF superfamily categorize them into two groups based on their signalling properties: those contain a death domain (DD) and others that engage TNFR-associated factors (TRAFs). There is a third group which lack a membrane-anchor domain and are proteolytically cleaved from the surface, or are anchored via glycolipid linkage and are termed "decoy receptors".

TNFRs comprise a binding domain which is positioned on the extracellular side of the cell membrane when the TNFR is expressed in a cell and a signalling domain which is expressed on the cytoplasmic side of the cell membrane when the TNFR is expressed in a cell.

TNFRSF9 (4-1BB), TNFRSF4 (OX40), TNFRSF5 (CD40) and TNFRSF14 (GITR) transmit survival signals to T-cells. TNFRSF7 (CD27) and TNFRSF14 (HVEM) are expressed by naïve T-cells. The expression of OX40 and 4-1BB is induced in response to antigen stimulation, these TNFRs have been proposed to be markers of effector T cells. Although CD27 and GITR can be constitutively expressed by conventional T cells, their expression is also strongly upregulated following T-cell activation, possibly in parallel with the upregulation of OX40 and 4-1BB expression.

The induction or upregulation of OX40, 4-1BB and GITR expression occurs within 24 hours following the recognition of antigen by and activation of naive T cells, and much more rapidly by memory T cells; the expression of these receptors can last for several hours or even days.

The TNF receptor TNFRSF35/Death receptor 3 (DR3) is activated by TL1A which is upregulated by inflamed tissue transiently and this interaction appears to be important for the late stage of T-cell activity after an established immune response.

CD40 is not expressed by T-cells, but CD40L is and CD40/CD40L is particularly important for B-cell differentiation and expansion.

TNFRSF11A (RANK) is not expressed by T-cells, but the RANK/RANK-L pathway is important to immune development as well as being a key pathway for osteoclast activity and is active during bone metastasis.

TNFRSF12A (Fn14) is not expressed by T-cells, but is expressed along with its ligand TWEAK in damaged or inflamed tissues and most cancers.

TNF Family Ligands

The TNF-related cytokines (TNF family ligands) are type II transmembrane proteins (intracellular N-terminus) with a short cytoplasmic tail (15 to 25 residues in length) and a larger extracellular region (~50 amino acids) containing the signature TNF homology domain where the receptor binding sites are located.

The TNF homology domain assembles into trimers, the functional unit of the ligand. Atomic analysis of several members of the family revealed that the ligands have a highly conserved tertiary structure folding into a β sheet sandwich, yet amino acid sequence conservation is limited to <35% among the family members.

The conserved residues defining this superfamily are primarily located within the internal β strands that form the molecular scaffold, which promote assembly into trimers. The residues in the loops between the external β-strands are variable and in specific loops make contact with the receptor.

A summary of TNFRs and their ligands is provided in Table 2.

TABLE 2

| Protein (member #) | Synonyms | Gene | Ligand(s) |
|---|---|---|---|
| Tumor necrosis factor receptor 1 | CD120a | TNFRSF1A | TNF-alpha (cachectin) |
| Tumor necrosis factor receptor 2 | CD120b | TNFRSF1B | TNF-alpha (cachectin) |
| Lymphotoxin beta receptor | CD18 | LTBR | Lymphotoxin beta (TNF-C) |
| OX40 | CD134 | TNFRSF4 | OX40L |
| CD40 | Bp50 | CD40 | CD154 |
| Fas receptor | Apo-1, CD95 | FAS | FasL |
| Decoy receptor 3 | TR6, M68 | TNFRSF6B | FasL, LIGHT, TL1A |
| CD27 | S152, Tp55 | CD27 | CD70, Siva |
| CD30 | Ki-1 | TNFRSF8 | CD153 |
| 4-1BB | CD137 | TNFRSF9 | 4-1BB ligand |
| Death receptor 4 | TRAILR1, Apo-2, CD261 | TNFRSF10A | TRAIL |
| Death receptor 5 | TRAILR2, CD262 | TNFRSF10B | TRAIL |
| Decoy receptor 1 | TRAILR3, LIT, TRID, CD263 | TNFRSF10C | TRAIL |
| Decoy receptor 2 | TRAILR4, TRUNDD, CD264 | TNFRSF10D | TRAIL |
| RANK | CD265 | TNFRSF11A | RANKL |
| Osteoprotegerin | OCIF, TR1 | TNFRSF11B | |
| TWEAK receptor | Fn14, CD266 | TNFRSF12A | TWEAK |
| TACI | IGAD2, CD267 | TNFRSF13B | APRIL, BAFF, CAMLG |
| BAFF receptor | CD268 | TNFRSF13C | BAFF |
| Herpesvirus entry mediator | ATAR, TR2, CD270 | TNFRSF14 | LIGHT |
| Nerve growth factor receptor | p75NTR, CD271 | NGFR | NGF, BDNF, NT-3, NT-4 |
| B-cell maturation antigen | TNFRSF13A, CD269 | TNFRSF17 | BAFF |
| Glucocorticoid-induced TNFR-related | AITR, CD357 | TNFRSF18 | GITR ligand |
| TROY | TAJ, TRADE | TNFRSF19 | unknown |
| Death receptor 6 | CD358 | TNFRSF21 | |
| Death receptor 3 | Apo-3, TRAMP, LARD, WS-1 | TNFRSF25 | TL1A |
| Ectodysplasin A2 receptor | XEDAR | EDA2R | EDA-A2 |

TNFR Binding Domain

The chimeric TNFR binding domain may be any domain which is capable of binding to a TNFR ligand. The binding domain may, for example, comprise the ligand binding domain of a TNFR or an antibody or a part thereof which is capable of binding to a TNFR ligand.

The binding domain may be capable of binding to a TNFR ligand as listed in Table 2. The binding domain may be capable of binding to a TNFR ligand which is present in a tumour microenvironment.

The binding domain may be capable of binding to a TNFR ligand selected from CD70, Receptor activator of NFκB (RANKL), TNF-related weak induce of apoptosis (TWEAK), TNFSF14 (LIGHT), TNFSF1 (LTA), BTLA (CD272), CD160, OX40L, 4-1BBL, CD30L, GITRL, TL1A and CD40L.

The binding domain may be capable of binding to CD70.
The binding domain may be capable of binding to RANKL.
The binding domain may be capable of binding to TWEAK.
The binding domain may be capable of binding to LIGHT, LTA, BTLA and/or CD160.

Figure 3:
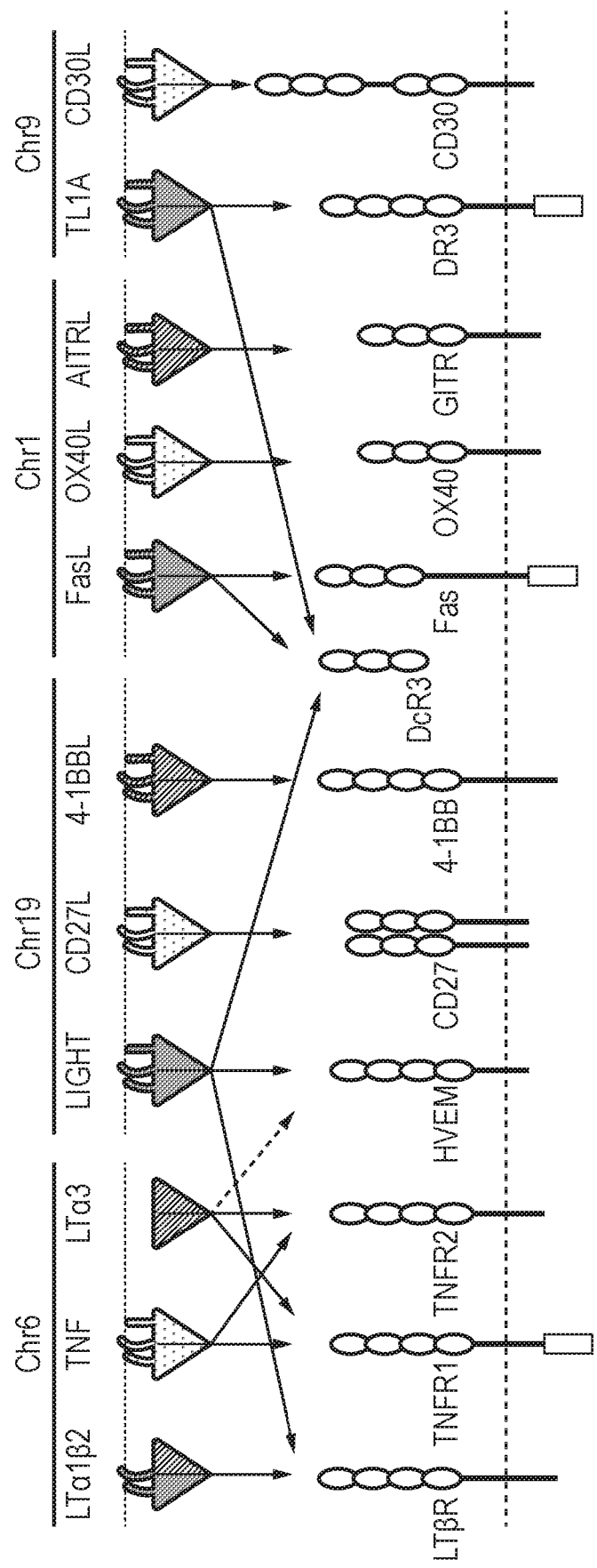
FIG. 3—Summary of the TNF superfamily

Suitably, the binding domain may comprise the ligand binding domain of a TNFR that binds to the TNFR ligand. A summary of TNFR/TNFR ligand interactions is provided in Table 2 and FIG. 3.

The binding domain may comprise the ligand binding domain selected from CD27, RANKL, Fn14, HVEM, OX40, 4-1BB, CD30, DR3, GITR or CD40 ligand binding domains.

The binding domain may comprise the ligand binding domain of CD27. CD27 expression is tightly controlled during early T-cell differentiation. CD70, the ligand of CD27, is widely expressed on activated T-cells, B-cells and macrophages. CD70 is also expressed on malignant cells such as B-cell lymphomas, leukaemia and gliomas and several other tumours.

An illustrative ligand binding domain of CD27 is shown as SEQ ID NO: 7. Suitably the ligand binding domain of CD27 may comprise SEQ ID NO: 7 or a variant thereof which has the ability to bind CD70. The SEQ ID NO: 7 variant may have at least 80, 85, 90, 95, 98 or 99% sequence identity to SEQ ID NO: 7 and have equivalent or improved CD70 binding capabilities as the sequence shown as SEQ ID NO: 7.

SEQ ID NO: 7
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIR

The binding domain may comprise the ligand binding domain of RANK. The RANK system serves an important role in the immune system, including in lymph-node development, lymphocyte differentiation, dendritic cell survival and T-cell activation, and tolerance induction. RANKL is expressed in several tissues and organs including: skeletal muscle, thymus, liver, colon, small intestine, adrenal gland, osteoblast, mammary gland epithelial cells, prostate and pancreas. A key role of the RANKL/RANK system is mediation of osteoclast-dependent bone remodelling and hence pathologic processes in metastatic disease to bone and is active in all osteolytic bone tumours which includes breast, lung and prostate cancer metastasis to bone and primary marrow disease—namely myeloma. RANK is not normally expressed on, for example, T-cells. Expression of the RANK ligand binding domain on a CAR T-cell, for example, may lead to wide activation particularly at sights of bone-marrow metastasis.

An illustrative ligand binding domain of RANK is shown as SEQ ID NO: 8. Suitably the ligand binding domain of RANK may comprise SEQ ID NO: 8 or a variant thereof which has the ability to bind RANKL. The SEQ ID NO: 8 variant may have at least 80, 85, 90, 95, 98 or 99% sequence identity to SEQ ID NO: 8 and have equivalent or improved RANKL binding capabilities as the sequence shown as SEQ ID NO: 8.

SEQ ID NO: 8
MAPRARRRRPLFALLLLCALLARLQVALQIAPPCTSEKHYEHLGRCCNKC

EPGKYMSSKCTTTSDSVCLPCGPDEYLDSWNEEDKCLLHKVCDTGKALVA

VVAGNSTTPRRCACTAGYHWSQDCECCRRNTECAPGLGAQHPLQLNKDTV

CKPCLAGYFSDAFSSTDKCRPWTNCTFLGKRVEHHGTEKSDAVCSSSLPA

RKPPNEPHVYLP

The binding domain may comprise the ligand binding domain of Fn14. Fn14 can be inducibly expressed on almost all tissues except lymphocytes. The ligand of Fn14 is TWEAK which is upregulated in tissues upon tissue injuries. TWEAK is produced by activated monocytes. TWEAK is also almost universally expressed in tumour microenvironments. Given that T-cells do not express Fn14, they cannot interpret TWEAK in the microenvironment. A chimeric TNFR which is capable of binding TWEAK will transmit activating and survival signals to, for example, a CAR T-cell within the tumour microenvironment.

An illustrative ligand binding domain of Fn14 is shown as SEQ ID NO: 9. Suitably the ligand binding domain of Fn14 may comprise SEQ ID NO: 9 or a variant thereof which has the ability to bind TWEAK. The SEQ ID NO: 9 variant may have at least 80, 85, 90, 95, 98 or 99% sequence identity to SEQ ID NO: 9 and have equivalent or improved TWEAK binding capabilities as the sequence shown as SEQ ID NO: 9.

SEQ ID NO: 9
MARGSLRRLLRLLVLGLWLALLRSVAGEQAPGTAPdwCSRGSSWSADLDK

CMDCASCRARPHSDFCLGCAAAPPAPFRLLWP

The binding domain may comprise the ligand binding domain of HVEM. While most TNF receptors have a single or at most two ligands, HVEM is unique in that it has multiple ligands. These include LIGHT, LTA, BTLA and CD160. Together, these ligands are expressed by a broad range of immune cells. HVEM is normally expressed on naïve and quiescent T-cells but not by activated ones. The expression of a chimeric TNFR comprising a HVEM ligand binding domain allows a CAR T-cell, for example, to receive multiple ligand signals during its activation.

An illustrative ligand binding domain of HVEM is shown as SEQ ID NO: 10. Suitably the ligand binding domain of HVEM may comprise SEQ ID NO: 10 or a variant thereof which has the ability to bind LIGHT, LTA, BTLA and/or CD160. The SEQ ID NO: 10 variant may have at least 80, 85, 90, 95, 98 or 99% sequence identity to SEQ ID NO: 10 and have equivalent or improved LIGHT, LTA, BTLA and CD160 binding capabilities as the sequence shown as SEQ ID NO: 10.

SEQ ID NO: 10
MEPPGDWGPPPWRSTPRTDVLRLVLYLTFLGAPCYAPALPSCKEDEYPVG

SECCPKCSPGYRVKEACGELTGTVCEPCPPGTYIAHLNGLSKCLQCQMCD

PAMGLRASRNCSRTENAVCGCSPGHFCIVQDGDHCAACRAYATSSPGQRV

QKGGTESQDTLCQNCPPGTFSPNGTLEECQHQTKCSWLVTKAGAGTSSSH

WV

The binding domain may comprise the ligand binding domain of DR3. DR3 costimulates T-cell activation, and signals through an intracytoplasmic death domain and the adapter protein TRADD (TNFR-associated death domain). TL1A costimulates T cells to produce a wide variety of cytokines and can promote expansion of activated and regulatory T cells in vivo. DR3 also enhances effector T-cell proliferation at the site of tissue inflammation in autoimmune disease models. A chimeric TNFR comprising a DR3 ligand binding domain allows activating and survival signals to be transmitted in, for example, a CAR T-cell within an inflamed tumour microenvironment.

An illustrative ligand binding domain of DR3 is shown as SEQ ID NO: 11. Suitably the ligand binding domain of DR3 may comprise SEQ ID NO: 11 or a variant thereof which has the ability to bind TL1A. The SEQ ID NO: 11 variant may have at least 80, 85, 90, 95, 98 or 99% sequence identity to SEQ ID NO: 11 and have equivalent or improved TL1A binding capabilities as the sequence shown as SEQ ID NO: 11.

SEQ ID NO: 11
MEQRPRGCAAVAAALLLVLLGARAQGGTRSPRCDCAGDFHKKIGLFCCRG

CPAGHYLKAPCTEPCGNSTCLVCPQDTFLAWENHHNSECARCQACDEQAS

QVALENCSAVADTRCGCKPGWFVECQVSQCVSSSPFYCQPCLDCGALHRH

TRLLCSRRDTDCGTCLPGFYEHGDGCVSCPTSTLGSCPERCAAVCGWRQ

As used herein, "antibody" means a polypeptide having an antigen binding site which comprises at least one complementarity determining region (CDR). The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'$_2$, Fv, single chain Fv (ScFv) fragment, Nanobody or single chain variable domain (which may be a VH or VL chain, having 3 CDRs). The antibody may be a bifunctional antibody. The antibody may be non-human, chimeric, humanised or fully human.

The chimeric TNFR binding domain may comprise a binding domain which is not derived from or based on an immunoglobulin. A number of "antibody mimetic" designed repeat proteins (DRPs) have been developed to exploit the binding abilities of non-antibody polypeptides. Such molecules include ankyrin or leucine-rich repeat proteins e.g. DARPins (Designed Ankyrin Repeat Proteins), Anticalins, Avimers and Versabodies.

The binding domain may "specifically bind" to the TNFR ligand as defined herein. As used herein, "specifically bind" means that the binding domain binds to the TNFR ligand but does not bind to other peptides, or binds at a lower affinity to other peptides.

The binding affinity between two molecules, e.g. a TNFR binding domain and a TNFR ligand, may be quantified for example, by determination of the dissociation constant (KD). The KD can be determined by measurement of the kinetics of complex formation and dissociation between the TNFR binding domain and a TNFR ligand, e.g. by the surface plasmon resonance (SPR) method (Biacore™). The rate constants corresponding to the association and the dissociation of a complex are referred to as the association rate constants ka (or kon) and dissociation rate constant kd. (or koff), respectively. KD is related to ka and kd through the equation KD=kd/ka.

Binding affinities associated with different molecular interactions, e.g. comparison of the binding affinity of different TNFR binding domains and a TNFR ligand, may be compared by comparison of the KD values for the individual TNFR binding domain and TNFR ligands.

TNFR Signalling Domain

The present chimeric TNFR further comprises a TNFR signalling domain.

Suitably, the TNFR signalling domain may be an activating signalling domain. The activating signalling domain may be capable of signalling via TNFR-associated factors (TRAFs).

TRAFs are adaptor proteins that couple TNFRs to signalling pathways. Six members of the TRAF family have been identified (TRAF1-6). All TRAF proteins share a C-terminal homology region termed the TRAF domain that is capable of binding to the cytoplasmic domain of receptors, and to other TRAF proteins. In addition, TRAFs 2-6 have RING and zinc finger motifs that are important for signalling downstream events.

The signalling domain may comprise a domain based on the signalling domain from a TNFR as listed in Table 2.

The signalling domain may comprise a domain based on the signalling domain from a TNFR selected from 4-1BB, OX40, GITR, CD27, CD40, DR3, HVEM, RANK and Fn14.

The signalling domain may comprise a domain based on the signalling domain from a TNFR selected from 4-1BB, OX40, GITR, CD27, CD40, and DR3.

The signalling domain may be based on the signalling domain of 4-1BB. 4-1BB is a co-stimulatory immune checkpoint molecule that provides costimulatory activity for activated T cells. 4-1BB signalling enhances T cell proliferation, IL-2 secretion, survival and cytolytic activity. 4-1BB has been shown to signal via TRAF2.

An illustrative 4-1BB signalling domain is shown as SEQ ID NO: 12. Suitably the 4-1BB signalling domain may comprise SEQ ID NO: 12 or a variant thereof which has the ability to provide a 4-1BB co-stimulatory signal following engagement of the chimeric TNFR binding domain. The SEQ ID NO: 12 variant may have at least 80, 85, 90, 95, 98 or 99% sequence identity to SEQ ID NO: 12 and have equivalent signalling properties to SEQ ID NO: 12.

SEQ ID NO: 12
KRGRKKLLYIFKQPFMRPVQTTQEEDGCSCRFPEEEEGGCEL

The signalling domain may be based on the signalling domain of OX40. OX40 is not constitutively expressed on resting naïve T cells, but is expressed after 24 to 72 hours following activation. OX40 signalling in T cells, for example, is important for T cell survival following activation and for the maintenance of cytokine production. The OX40 signalling domain binds TRAF2, 3 and 5 and PI3 kinase.

An illustrative OX40 signalling domain is shown as SEQ ID NO: 13. Suitably the OX40 signalling domain may comprise SEQ ID NO: 13 or a variant thereof which has the ability to provide a OX40 co-stimulatory signal following engagement of the chimeric TNFR binding domain. The SEQ ID NO: 13 variant may have at least 80, 85, 90, 95, 98 or 99% sequence identity to SEQ ID NO: 13 and have equivalent signalling properties to SEQ ID NO: 13.

SEQ ID NO: 13
RDQRLPPDAHKPPGGGSFRTPIQEEQADAHSTLAKI

The signalling domain may be based on the signalling domain of GITR. GITR expression is increased following T cell activation and is involved in the regulation of CD3-driven T-cell activation and programmed cell death. In particular, it is involved in inhibiting the suppressive activity of T-regulatory cells and extending the survival of T-effector cells An illustrative GITR signalling domain is shown as SEQ ID NO: 14. Suitably the GITR signalling domain may comprise SEQ ID NO: 14 or a variant thereof which has the ability to provide a GITR co-stimulatory signal following engagement of the chimeric TNFR binding domain. The SEQ ID NO: 14 variant may have at least 80, 85, 90, 95, 98 or 99% sequence identity to SEQ ID NO: 14 and have equivalent signalling properties to SEQ ID NO: 14.

SEQ ID NO: 14
QLGLHIWQLRSQCMWPRETQLLLEVPPSTEDARSCQFPEEERGERSAEEK

GRLGDLWV

The signalling domain may be based on the signalling domain of CD27. CD27 is required for generation and long-term maintenance of T cell immunity. It binds to ligand CD70, and plays a key role in regulating B-cell activation and immunoglobulin synthesis. This receptor transduces signals that lead to the activation of NF-κB and MAPK8/JNK. Adaptor proteins TRAF2 and TRAF5 have been shown to mediate the signalling process of this receptor.

An illustrative CD27 signalling domain is shown as SEQ ID NO: 15. Suitably the CD27 signalling domain may comprise SEQ ID NO: 15 or a variant thereof which has the ability to provide a CD27 co-stimulatory signal following engagement of the chimeric TNFR binding domain. The SEQ ID NO: 15 variant may have at least 80, 85, 90, 95, 98 or 99% sequence identity to SEQ ID NO: 15 and have equivalent signalling properties to SEQ ID NO: 15.

SEQ ID NO: 15
QRRKYRSNKGESPVEPAEPCHYSCPREEEGSTIPIQEDYRKPEPACSP

The signalling domain may be based on the signalling domain of CD40. CD40 is a costimulatory protein found on antigen presenting cells and is required for their activation. The binding of CD154 (CD40L) on TH cells to CD40 activates antigen presenting cells and induces a variety of downstream effects. The CD40 signalling domain interacts with TRAF1, TRAF2 and TRAF6.

An illustrative CD40 signalling domain is shown as SEQ ID NO: 16. Suitably the CD40 signalling domain may comprise SEQ ID NO: 16 or a variant thereof which has the ability to provide a CD40 co-stimulatory signal following engagement of the chimeric TNFR binding domain. The SEQ ID NO: 16 variant may have at least 80, 85, 90, 95, 98 or 99% sequence identity to SEQ ID NO: 16 and have equivalent signalling properties to SEQ ID NO: 16.

SEQ ID NO: 16
KKVAKKPTNKAPHPKQEPQEINFPDDLPGSNTAAPVQETLHGCQPVTQED

GKESRISVQERQ

The signalling domain may be based on the signalling domain of DR3.

An illustrative DR3 signalling domain is shown as SEQ ID NO: 17. Suitably the DR3 signalling domain may comprise SEQ ID NO: 17 or a variant thereof which has the ability to provide a DR3 co-stimulatory signal following engagement of the chimeric TNFR binding domain. The SEQ ID NO: 17 variant may have at least 80, 85, 90, 95, 98 or 99% sequence identity to SEQ ID NO: 17 and have equivalent signalling properties to SEQ ID NO: 17.

SEQ ID NO: 17
TYTYRHCWPHKPLVTADEAGMEALTPPPATHLSPLDSAHTLLAPPDSSEK

ICTVQLVGNSWTPGYPETQEALCPQVTWSWDQLPSRALGPAAAPTLSPES

PAGSPAMMLQPGPQLYDVMDAVPARRWKEFVRTLGLREAEIEAVEVEIGR

FRDQQYEMLKRWRQQQPAGLGAVYAALERMGLDGCVEDLRSRLQRGP

Assays which may be used to determine that a variant signalling domain as described herein is capable of signalling in the same manner as the parent sequence include standard immunological assays which characterize productive T-cell function. These include, for example, flow-cytometric analysis of differentiation, exhaustion and activation; cytotoxicity assays; proliferation assays; measurement of cytokines released and transcriptional profiling (RNAseq).

Suitably, the signalling domain of the present chimeric TNFR is not capable of providing "signal 1" when expressed in a T cell, for example. Thus, the chimeric TNFR is capable of binding a TNFR ligand, but engagement of the chimeric TNFR does not result in productive signal 1 signalling in the cell. In other words, engagement of the chimeric TNFR is capable of providing co-stimulatory signalling to the cell, but is not sufficient to induce full activation of the engineered cell (as it does not provide signal 1).

Thus, in the cell of the present invention, signal 1 is provided upon engagement of the CAR or transgenic TCR and further co-stimulatory signals are provided upon engagement of the chimeric TNFR.

The signalling domain of the chimeric TNFR may consist essential of or consist of a TNFR signalling domain as described herein.

Suitably, the chimeric TNFR does not comprise a CD3 endodomain. Suitably, the chimeric TNFR does not comprise a CD3zeta endodomain (an illustrative CD3zeta endodomain is shown as SEQ ID NO: 31).

Transmembrane Domain

The chimeric TNFR further comprises a transmembrane domain that spans the membrane. The transmembrane domain may be any protein structure which is thermodynamically stable in a membrane. This is typically an alpha helix comprising of several hydrophobic residues. The transmembrane domain of any transmembrane protein can be used to supply a transmembrane portion. The presence and span of a transmembrane domain of a protein can be determined by those skilled in the art using the TMHMM algorithm (www.cbs.dtu.dk/services/TMHMM-2.0). Further, given that the transmembrane domain of a protein is a relatively simple structure, i.e., a polypeptide sequence predicted to form a hydrophobic alpha helix of sufficient length to span the membrane, an artificially designed TM domain may also be used (U.S. Pat. No. 7,052,906 B1 describes transmembrane components).

The transmembrane domain may comprise a hydrophobic alpha helix. The transmembrane domain may be derived from CD28, which gives good receptor stability. The transmembrane domain may comprise the sequence shown as SEQ ID NO: 18 or a variant thereof having at least 80% sequence identity.

```
                               SEQ ID NO: 18
FWVLVVVGGVLACYSLLVTVAFIIFWV
```

The variant may have at least 80, 85, 90, 95, 98 or 99% sequence identity with SEQ ID NO: 18, provided that the variant sequence retains the capacity to traverse the membrane.

The transmembrane domain may be based on the transmembrane domain from a TNFR, for example a TNFR as described herein. Suitably the transmembrane domain may be based on the same TNFR as the signalling domain present in the chimeric TNFR.

Suitably, the transmembrane domain may comprise any one of SEQ ID NO: 19-24 or a variant thereof having at least 80% sequence identity. The variant may have at least 80, 85, 90, 95, 98 or 99% sequence identity with SEQ ID NO: 19-24, provided that the variant sequence retains the capacity to traverse the membrane.

```
(4-1BB transmembrane domain)
                               SEQ ID NO: 19
IISFFLALTSTALLFLLFFLTLRFSVV (DR3 transmembrane domain)
                               SEQ ID NO: 20
MFWVQVLLAGLVVPLLLGATL (OX40 transmembrane domain)
                               SEQ ID NO: 21
VAAILGLGLVLGLLGPLAILL (GITR transmembrane domain)
                               SEQ ID NO: 22
LGWLTVVLLAVAACVLLLTSA (CD70 transmembrane domain)
                               SEQ ID NO: 23
VLRAALVPLVAGLVICLVVCI (CD40 transmembrane domain)
                               SEQ ID NO: 24
ALVVIPIIFGILFAILLVLVFI
```

Any combination of a binding domain which binds a TNFR ligand for a first TNFR and a signalling domain from a second TNFR may be appropriate for the present invention.

Without wishing to be bound by theory, the following combination may be considered to have particular benefits for the function of an engineered T-cell, for example. For instance, non-physiological interactions with ligands for HVEM, CD27, RANK and Fn14 are quite distinct from physiological TNF ligand interactions. Regarding signalling domains, 4-1BB is known to provide particularly important co-stimulatory signals for T cell function.

The present chimeric TNFR may comprise a binding domain which binds to a ligand of HVEM, CD27, RANK, DR3 or Fn14 and the 4-1BB signalling domain.

The chimeric TNFR may comprise the HVEM binding domain and the 4-1BB signalling domain. An illustrative HVEM/4-1BB chimeric TNFR is shown as SEQ ID NO: 2. Suitably the HVEM/4-1BB chimeric TNFR may comprise SEQ ID NO: 2 or a variant thereof which has the ability to bind a HVEM ligand and provide a 4-1BB co-stimulatory signal following engagement of the chimeric TNFR binding domain. The SEQ ID NO: 2 variant may have at least 80, 85, 90, 95, 98 or 99% sequence identity to SEQ ID NO: 2 and have equivalent signalling properties to SEQ ID NO: 2.

```
                                       SEQ ID NO: 2
MEPPGDWGPPPWRSTPRTDVLRLVLYLTFLGAPCYAPALPSCKEDEYPVG

SECCPKCSPGYRVKEACGELTGTVCEPCPPGTYIAHLNGLSKCLQCQMCD

PAMGLRASRNCSRTENAVCGCSPGHFCIVQDGDHCAACRAYATSSPGQRV

QKGGTESQDTLCQNCPPGTFSPNGTLEECQHQTKCSWLVTKAGAGTSSSH

WVIISFFLALTSTALLFLLFFLTLRFSVVKRGRKKLLYIFKQPFMRPVQT

TQEEDGCSCRFPEEEEGGCEL
```

HVEM ectodomain is in normal text (Uniprot; Q92956)
4-1BB transmembrane domain is in bold (Uniprot; Q07011)
4-1BB endodomain is in italics (Uniprot; Q07011)

The chimeric TNFR may comprise the CD27 ligand binding domain and the 4-1BB signalling domain. An illustrative HVEM/4-1BB chimeric TNFR is shown as SEQ ID NO: 3. Suitably the CD27/4-1BB chimeric TNFR may comprise SEQ ID NO: 3 or a variant thereof which has the ability to bind a CD27 ligand and provide a 4-1BB co-stimulatory signal following engagement of the chimeric TNFR binding domain. The SEQ ID NO: 3 variant may have at least 80, 85, 90, 95, 98 or 99% sequence identity to SEQ ID NO: 3 and have equivalent signalling properties to SEQ ID NO: 3.

```
                                       SEQ ID NO: 3
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIRIISFFLALT

STALLFLLFFLTLRFSVVKRGRKKLLYIFKQPFMRPVQTTQEEDGCSCRF

PEEEEGGCEL
```

CD27 ectodomain is in normal text (Uniprot; P26842)
4-1BB transmembrane domain is in bold (Uniprot; Q07011)
4-1BB endodomain is in italics (Uniprot; Q07011)

The chimeric TNFR may comprise the RANK ligand binding domain and the 4-1BB signalling domain. An illustrative RAN K/4-1BB chimeric TNFR is shown as SEQ ID NO: 4. Suitably the RANK/4-1BB chimeric TNFR may comprise SEQ ID NO: 4 or a variant thereof which has the ability to bind a RANK ligand and provide a 4-1BB costimulatory signal following engagement of the chimeric TNFR binding domain. The SEQ ID NO: 4 variant may have at least 80, 85, 90, 95, 98 or 99% sequence identity to SEQ ID NO: 4 and have equivalent signalling properties to SEQ ID NO: 4.

SEQ ID NO: 4
MAPRARRRRPLFALLLLCALLARLQVALQIAPPCTSEKHYEHLGRCCNKC

EPGKYMSSKCTTTSDSVCLPCGPDEYLDSWNEEDKCLLHKVCDTGKALVA

VVAGNSTTPRRCACTAGYHWSQDCECCRRNTECAPGLGAQHPLQLNKDTV

CKPCLAGYFSDAFSSTDKCRPWTNCTFLGKRVEHHGTEKSDAVCSSSLPA

RKPPNEPHVYLPIISFFLALTSTALLFLLFFLTLRFSVVKRGRKKLLYIF

KQPFMRPVQTTQEEDGCSCRFPEEEEGGCEL

RANK ectodomain is in normal text (Uniprot; Q9Y6Q6)
4-1BB transmembrane domain is in bold (Uniprot; Q07011)
4-1BB endodomain is in italics (Uniprot; Q07011)

The chimeric TNFR may comprise the Fn14 ligand binding domain and the 4-1BB signalling domain. An illustrative Fn14/4-1BB chimeric TNFR is shown as SEQ ID NO: 5. Suitably the Fn14/4-1BB chimeric TNFR may comprise SEQ ID NO: 5 or a variant thereof which has the ability to bind a Fn14 ligand and provide a 4-1BB co-stimulatory signal following engagement of the chimeric TNFR binding domain. The SEQ ID NO: 5 variant may have at least 80, 85, 90, 95, 98 or 99% sequence identity to SEQ ID NO: 5 and have equivalent signalling properties to SEQ ID NO: 5.

SEQ ID NO: 5
MARGSLRRLLRLLVLGLWLALLRSVAGEQAPGTAPdwCSRGSSWSADLDK

CMDCASCRARPHSDFCLGCAAAPPAPFRLLWPIISFFLALTSTALLFLLF

FLTLRFSVVKRGRKKLLYIFKOPFMRPVOTTQEEDGCSCRFPEEEEGGCE

L

Fn14 ectodomain is in normal text (Uniprot; Q9NP84)
4-1BB transmembrane domain is in bold (Uniprot; Q07011)
4-1BB endodomain is in italics (Uniprot; Q07011)

The chimeric TNFR may comprise the DR3 ligand binding domain and the 4-1BB signalling domain. An illustrative DR3/4-1BB chimeric TNFR is shown as SEQ ID NO: 1. Suitably the DR3/4-1BB chimeric TNFR may comprise SEQ ID NO: 1 or a variant thereof which has the ability to bind a DR3 ligand and provide a 4-1BB co-stimulatory signal following engagement of the chimeric TNFR binding domain. The SEQ ID NO: 1 variant may have at least 80, 85, 90, 95, 98 or 99% sequence identity to SEQ ID NO: 1 and have equivalent signalling properties to SEQ ID NO: 1.

SEQ ID NO: 1
MEQRPRGCAAVAAALLLVLLGARAQGGTRSPRCDCAGDFHKKIGLFCCRG

CPAGHYLKAPCTEPCGNSTCLVCPQDTFLAWENHHNSECARCQACDEQAS

QVALENCSAVADTRCGCKPGWFVECQVSQCVSSSPFYCQPCLDCGALHRH

TRLLCSRRDTDCGTCLPGFYEHGDGCVSCPTSTLGSCPERCAAVCGWRQI

ISFFLALTSTALLFLLFFLTLRFSVVKRGRKKLLYIFKOPFMRPVQTTQE

EDGCSCRFPEEEEGGCEL

TNFRSF25 (DR3) ectodomain is in normal text (Uniprot; Q93038)
4-1BB transmembrane domain is in bold (Uniprot; Q07011)
4-1BB endodomain is in italics (Uniprot; Q07011)

The chimeric TNFR may comprise the CD27 binding domain and the DR3 signalling domain. An illustrative CD27/DR3 chimeric TNFR is shown as SEQ ID NO: 6. Suitably the CD27/DR3 chimeric TNFR may comprise SEQ ID NO: 6 or a variant thereof which has the ability to bind a CD27 ligand and provide a DR3 co-stimulatory signal following engagement of the chimeric TNFR binding domain. The SEQ ID NO: 6 variant may have at least 80, 85, 90, 95, 98 or 99% sequence identity to SEQ ID NO: 6 and have equivalent signalling properties to SEQ ID NO: 6.

SEQ ID NO: 6
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIRMFWVQVLLA

GLVVPLLLGATLTYTYRHCWPHKPLVTADEAGMEALTPPPATHLSPLDSA

HTLLAPPDSSEKICTVQLVGNSWTPGYPETQEALCPQVTWSWDQLPSRAL

GPAAAPTLSPESPAGSPAMMLQPGPQLYDVMDAVPARRWKEFVRTLGLRE

AEIEAVEVEIGRFRDQQYEMLKRWRQQQPAGLGAVYAALERMGLDGCVED

LRSRLQRGP

CD27 ectodomain is in normal text (Uniprot; P26842)
TNFRSF25 transmembrane domain is in bold text (Uniprot; Q93038)
TNFRSF25 endodomain is in italic text (Uniprot; Q93038)

In one aspect, the present invention provides a chimeric TNFR as defined herein.

Suitably, the cell of the invention may comprise a plurality of different chimeric TNFRs as provided by the present invention. For example, the cell may comprise two, three, four or five different chimeric TNFRs of the invention. By "different TNFRs" it is meant that a first chimeric TNFR may comprise a different ligand binding domain and/or a different signalling domain compared to a second TNFR.

TNFR Over-Expression

In one aspect the present invention provides a cell which comprises; (i) a chimeric antigen receptor (CAR) or a transgenic T-cell receptor (TCR); and (ii) an exogenous polynucleotide expressing a TNF receptor (TNFR) which is capable of providing a co-stimulatory to the cell following binding of a ligand to the TNFR ligand binding domain.

As used herein, the term "exogenous polynucleotide" means that the polynucleotide which expresses the TNFR is not part of the endogenous genome of the cell. For example, the exogenous polynucleotide may be an engineered nucleic acid construct or a vector.

The exogenous polynucleotide may express CD27, CD40, DR3, HVEM, RANK or Fn14. In one embodiment the exogenous polynucleotide may express CD27 or CD40.

The cell may be any cell as defined herein. Suitably, the cell may be a T-cell, a natural killer (NK) cell or a cytokine induced killer cell.

The ligands for CD27, CD40, DR3, HVEM, RANK and Fn14 are typically present in the inflammatory tumour microenvironment. However, these TNFRs are either expressed by—for example—T cells in a tightly regulated manner (e.g. during particular periods of T cell development) or not generally expressed by T cells.

Accordingly, exogenous expression of CD27, CD40, DR3, HVEM, RANK or Fn14 in a T cell, for example, may provide similar advantages to the chimeric TNFR of the present invention. For example, following engagement by the TNFR ligand which typically binds to the TNFR, the TNFR expressed from the exogenous polynucleotide is capable of transmitting a co-stimulatory signal. This enables the tight temporal and/or spatial control of TNFR signalling to be decoupled in order to provide improved survival signals for engineered cells, for example CAR T cells.

By way of example, in lymphomas CD70 is abundant so a cell over-expressing CD27 may be provided; in lytic bone metastasis RANKL is abundant so a cell over-expressing RANK might be provided. In solid cancers, TWEAK is abundant so a cell over-expressing may be provided.

As used herein, "over-expressed" or "over-expression" refers to an increased level of expression of the TNFR compared to a corresponding, unmodified cell which does not comprise an exogenous polynucleotide which is capable of expressing the TNFR. Expression levels may be determined by methods which are known in the art, for example, real-time quantitative PCR, western blot and/or flow cytometry, The cell of invention may express at least 1.5-, at least 2-, at least 5-, at least 5-, at least 10-, at least 20-, at least 50-, or at least 100-fold greater levels of the TNFR compared to a corresponding, unmodified cell.

Suitably, the TNFR expressed by the exogenous polynucleotide may not be detectable in a corresponding, unmodified cell.

Illustrative amino acid sequences for CD27, CD40, DR3, HVEM, RANK and Fn14 are shown as SEQ ID NO: 25-30. The exogenous polynucleotide sequence may be capable of expressing a polypeptide comprising the sequence shown as one of SEQ ID NO: 25-30 or a variant thereof which has at least 80% sequence identity to one of SEQ ID NO: 25-30.

The variant may have at least 80, 85, 90, 95, 98 or 99% sequence identity to SEQ ID NO: 25-30 and have equivalent ligand binding and signalling properties to the corresponding parent SEQ ID NO: 25-30.

The variant may have at least 80, 85, 90, 95, 98 or 99% sequence identity to SEQ ID NO: 25 and have equivalent ligand binding and signalling properties to the corresponding parent SEQ ID NO: 25.

The variant may have at least 80, 85, 90, 95, 98 or 99% sequence identity to SEQ ID NO: 26) and have equivalent ligand binding and signalling properties to the corresponding parent SEQ ID NO: 26.

(CD27)

SEQ ID NO: 25

MPEEGSGCSVRRRPYGCVLRAALVPLVAGLVICLVVCIQRFAQAQQQLPLESLGWDVAELQLNHTGPQQDPRLYW

QGGPALGRSFLHGPELDKGQLRIHRDGIYMVHIQVTLAICSSTTASRHHPTTLAVGICSPASRSISLLRLSFHQG

CTIASQRLTPLARGDTLCTNLTGTLLPSRNTDETFFGVQWVRP (CD40)

SEQ ID NO: 26

MVRLPLQCVLWGCLLTAVHPEPPTACREKQYLINSQCCSLCQPGQKLVSDCTEFTETECLPCGESEFLDTWNRET

HCHQHKYCDPNLGLRVQQKGTSETDTICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPIIFGILFAILLVLVFIKKVAKKPTNK

APHPKQEPQEINFPDDLPGSNTAAPVQETLHGCQPVTQEDGKESRISVQERQ (DR3)

SEQ ID NO: 27

MEQRPRGCAAVAAALLLVLLGARAQGGTRSPRCDCAGDFHKKIGLFCCRGCPAGHYLKAPCTEPCGNSTCLVCPQ

DTFLAWENHHNSECARCQACDEQASQVALENCSAVADTRCGCKPGWFVECQVSQCVSSSPFYCQPCLDCGALHRH

TRLLCSRRDTDCGTCLPGFYEHGDGCVSCPTSTLGSCPERCAAVCGWRQMFWVQVLLAGLVVPLLLGATLTYTYR

HCWPHKPLVTADEAGMEALTPPPATHLSPLDSAHTLLAPPDSSEKICTVQLVGNSWTPGYPETQEALCPQVTWSW

DQLPSRALGPAAAPTLSPESPAGSPAMMLQPGPQLYDVMDAVPARRWKEFVRTLGLREAEIEAVEVEIGRFRDQQ

YEMLKRWRQQQPAGLGAVYAALERMGLDGCVEDLRSRLQRGP (HVEM)

SEQ ID NO: 28

MEPPGDWGPPPWRSTPKTDVLRLVLYLTFLGAPCYAPALPSCKEDEYPVGSECCPKCSPGYRVKEACGELTGTVC

EPCPPGTYIAHLNGLSKCLQCQMCDPAMGLRASRNCSRTENAVCGCSPGHFCIVQDGDHCAACRAYATSSPGQRV

QKGGTESQDTLCQNCPPGTFSPNGTLEECQHQTKCSWLVTKAGAGTSSSHWVWWFLSGSLVIVIVCSTVGLIICV

KRRKPRGDVVKVIVSVQRKRQEAEGEATVIEALQAPPDVTTVAVEETIPSFTGRSPNH (RANK)

SEQ ID NO: 29

MAPRARRRRPLFALLLLCALLARLQVALQIAPPCTSEKHYEHLGRCCNKCEPGKYMSSKCTTTSDSVCLPCGPDE

YLDSWNEEDKCLLHKVCDTGKALVAVVAGNSTTPRRCACTAGYHWSQDCECCRRNTECAPGLGAQHPLQLNKDTV

```
-continued
CKPCLAGYFSDAFSSTDKCRPWTNCTFLGKRVEHHGTEKSDAVCSSSLPARKPPNEPHVYLPGLIILLLFASVAL

VAAIIFGVCYRKKGKALTANLWHWINEACGRLSGDKESSGDSCVSTHTANFGQQGACEGVLLLTLEEKTFPEDMC

YPDQGGVCQGTCVGGGPYAQGEDARMLSLVSKTEIEEDSFRQMPTEDEYMDRPSQPTDQLLFLTEPGSKSTPPFS

EPLEVGENDSLSQCFTGTQSTVGSESCNCTEPLCRTDWTPMSSENYLQKEVDSGHCPHWAASPSPNWADVCTGCR

NPPGEDCEPLVGSPKRGPLPQCAYGMGLPPEEEASRTEARDQPEDGADGRLPSSARAGAGSGSSPGGQSPASGNV

TGNSNSTFISSGQVMNFKGDIIVVYVSQTSQEGAAAAAEPMGRPVQEETLARRDSFAGNGPRFPDPCGGPEGLRE

PEKASRPVQEQGGAKA (Fn14)
                                                    SEQ ID NO: 30
MARGSLRRLLRLLVLGLWLALLRSVAGEQAPGTAPCSRGSSWSADLDKCMDCASCRARPHSDFCLGCAAAPPAPF

RLLWPILGGALSLTFVLGLLSGFLVWRRCRRREKFTTPIEETGGEGCPAVALIQ
```

The exogenous polynucleotide may be provided as a nucleic acid construct or a vector, for example. Nucleic acid constructs and vectors may be introduced into a cell using methods which are known in the art, for example by viral transduction.

In one aspect the present invention provides a nucleic acid construct which comprises: (i) a first nucleic acid sequence which encodes i) a chimeric antigen receptor (CAR) or a transgenic T-cell receptor (TCR); and (ii) a second nucleic acid sequence which is an exogenous polynucleotide capable of expressing a TNF receptor (TNFR) which is capable of providing a co-stimulatory to the cell following binding of a ligand to the TNFR ligand binding domain.

The exogenous polynucleotide expressing a TNFR may be an exogenous polynucleotide as defined herein.

The present invention further provides a kit comprising: (i) a first nucleic acid sequence which encodes i) a chimeric antigen receptor (CAR) or a transgenic T-cell receptor (TCR); and (ii) a second nucleic acid sequence which is an exogenous polynucleotide capable of expressing a TNF receptor (TNFR) which is capable of providing a co-stimulatory to the cell following binding of a ligand to the TNFR ligand binding domain.

The first nucleic acid sequence and second nucleic acid sequence may be separated by a co-expression site which enables expression of the first nucleic acid sequence which encodes a chimeric antigen receptor (CAR) or a transgenic T-cell receptor (TCR); and the second nucleic acid sequence which is an exogenous polynucleotide capable of expressing a TNF receptor (TNFR) which is capable of providing a co-stimulatory to the cell following binding of a ligand to the TNFR ligand binding domain from a single nucleic acid construct.

Suitably, the co-expression site may be a co-expression site as defined herein.

The present invention also provides a vector, or kit of vectors which comprises one or more nucleic acid sequence(s) or nucleic acid construct(s) which comprises (i) a first nucleic acid sequence which encodes i) a chimeric antigen receptor (CAR) or a transgenic T-cell receptor (TCR); and (ii) a second nucleic acid sequence which is an exogenous polynucleotide capable of expressing a TNF receptor (TNFR) which is capable of providing a co-stimulatory to the cell following binding of a ligand to the TNFR ligand binding domain.

The vector may be a vector as defined herein.

The nucleic acid construct or vector may be for use in therapy as described herein.

Chimeric Antigen Receptor (CAR)

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site or on a ligand for the target antigen. A spacer domain may be necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 4-1BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Antigen Binding Domain

The antigen-binding domain is the portion of a classical CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Transmembrane Domain

The transmembrane domain is the sequence of a classical CAR that spans the membrane. It may comprise a hydrophobic alpha helix. The transmembrane domain may be derived from CD28, which gives good receptor stability.

Signal Peptide

The CAR may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

Spacer Domain

The CAR may comprise a spacer sequence to connect the antigen-binding domain with the transmembrane domain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Intracellular Signalling Domain

The intracellular signalling domain is the signal-transmission portion of a classical CAR.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

The intracellular signalling domain may be or comprise a T cell signalling domain.

The intracellular signalling domain may comprise one or more immunoreceptor tyrosine-based activation motifs (ITAMs). An ITAM is a conserved sequence of four amino acids that is repeated twice in the cytoplasmic tails of certain cell surface proteins of the immune system. The motif contains a tyrosine separated from a leucine or isoleucine by any two other amino adds, giving the signature YxxL/I. Two of these signatures are typically separated by between 6 and 8 amino acids in the tail of the molecule ($YxxL/Ix_{(6-8)}YxxL/I$). ITAMs are important for signal transduction in immune cells. Hence, they are found in the tails of important cell signalling molecules such as the CD3 and ζ-chains of the T cell receptor complex, the CD79 alpha and beta chains of the B cell receptor complex, and certain Fc receptors. The tyrosine residues within these motifs become phosphorylated following interaction of the receptor molecules with their ligands and form docking sites for other proteins involved in the signalling pathways of the cell.

The intracellular signalling domain component may comprise, consist essentially of, or consist of the CD3-ζ endodomain, which contains three ITAMs. Classically, the CD3-ζ endodomain transmits an activation signal to the T cell after antigen is bound. However, in the context of the present invention, the CD3-ζ endodomain transmits an activation signal to the T cell after the MHC/peptide complex comprising the engineered B2M binds to a TCR on a different T cell.

The intracellular signalling domain may comprise additional co-stimulatory signalling. For example, 4-1BB (also known as CD137) can be used with CD3-ζ, or CD28 and OX40 can be used with CD3-ζ to transmit a proliferative/survival signal.

Accordingly, intracellular signalling domain may comprise the CD3-ζ endodomain alone, the CD3-ζ endodomain in combination with one or more co-stimulatory domains selected from 4-1BB, CD28 or OX40 endodomain, and/or a combination of some or all of 4-1BB, CD28 or OX40.

The endodomain may comprise one or more of the following: an ICOS endodomain, a CD2 endodomain, a CD27 endodomain, or a CD40 endodomain.

The endodomain may comprise the sequence shown as SEQ ID NO: 31 to 34 or a variant thereof having at least 80, 85, 90, 95, 98 or 99% sequence identity, provided that the variant sequence retains the capacity to transmit an activating signal to the cell.

The percentage identity between two polypeptide sequences may be readily determined by programs such as BLAST, which is freely available at blast.ncbi.nlm.nih.gov. Suitably, the percentage identity is determined across the entirety of the reference and/or the query sequence.

CD3-ζ endodomain

SEQ ID NO: 31
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

-continued 4-1BB and CD3-ζ endodomains
SEQ ID NO: 32
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPQRRKNPQEGLYNELQKDKMAEAYSEIGMKGERRRGKGHDGLYQGLS

TATKDTYDALHMQALPPR

CD28 and CD3-ζ endodomains
SEQ ID NO: 33
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

CD28, OX40 and CD3-ζ endodomains
SEQ ID NO: 34
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

Suitably, the CAR may have the general format: antigen-binding domain-TCR element.

As used herein "TCR element" means a domain or portion thereof of a component of the TCR receptor complex. The TCR element may comprise (e.g. have) an extracellular domain and/or a transmembrane domain and/or an intracellular domain e.g. intracellular signalling domain of a TCR element.

The TCR element may selected from TCR alpha chain, TCR beta chain, a CD3 epsilon chain, a CD3 gamma chain, a CD3 delta chain, CD3 epsilon chain.

Suitably, the TCR element may comprise the extracellular domain of the TCR alpha chain, TCR beta chain, a CD3 epsilon chain, a CD3 gamma chain, a CD3 delta chain, or CD3 epsilon chain.

Suitably, the TCR element may comprise the transmembrane domain of the TCR alpha chain, TCR beta chain, a CD3 epsilon chain, a CD3 gamma chain, a CD3 delta chain, or CD3 epsilon chain.

Suitably, the TCR element may comprise the intracellular domain of the TCR alpha chain, TCR beta chain, a CD3 epsilon chain, a CD3 gamma chain, a CD3 delta chain, or CD3 epsilon chain.

Suitably, the TCR element may comprise the TCR alpha chain, TCR beta chain, a CD3 epsilon chain, a CD3 gamma chain, a CD3 delta chain, or CD3 epsilon chain.

Transgenic T-Cell Receptor (TCR)

The T-cell receptor (TCR) is a molecule found on the surface of T cells which is responsible for recognizing fragments of antigen as peptides bound to major histocompatibility complex (MHC) molecules.

The TCR is a heterodimer composed of two different protein chains. In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively).

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using a vector. For example the genes for engineered TCRs may be reintroduced into autologous T cells and transferred back into patients for T cell adoptive therapies. Such 'heterologous' TCRs may also be referred to herein as 'transgenic TCRs'.

Cell

The cell of the present invention may be an immune effector cell, such as a T-cell, a natural killer (NK) cell or a cytokine induced killer cell.

The T cell may be an alpha-beta T cell or a gamma-delta T cell.

The cell may be derived from a patient's own peripheral blood (1st party), or in the setting of a haematopoietic stem cell transplant from donor peripheral blood (2nd party), or peripheral blood from an unconnected donor (3rd party). T or NK cells, for example, may be activated and/or expanded prior to being transduced with nucleic acid molecule(s) encoding the polypeptides of the invention, for example by treatment with an anti-CD3 monoclonal antibody.

Alternatively, the cell may be derived from ex vivo differentiation of inducible progenitor cells or embryonic progenitor cells to T cells. Alternatively, an immortalized T-cell line which retains its lytic function may be used.

The cell may be a haematopoietic stem cell (HSC). HSCs can be obtained for transplant from the bone marrow of a suitably matched donor, by leukopheresis of peripheral blood after mobilization by administration of pharmacological doses of cytokines such as G-CSF [peripheral blood stem cells (PBSCs)], or from the umbilical cord blood (UCB) collected from the placenta after delivery. The marrow, PBSCs, or UCB may be transplanted without processing, or the HSCs may be enriched by immune selection with a monoclonal antibody to the CD34 surface antigen.

The cell of the present invention is an engineered cell. Accordingly, the CAR or transgenic TCR and the chimeric TNFR are not naturally expressed by a corresponding, unmodified cell—for example an unmodified alpha-beta T cell, a NK cell, a gamma-delta T cell or cytokine-induced killer cell.

Nucleic Acid Construct/Kit of Nucleic Acid Sequences

The present invention provides a nucleic acid construct which comprises: (i) a first nucleic acid sequence which encodes i) a chimeric antigen receptor (CAR) or a transgenic T-cell receptor (TCR); and (ii) a second nucleic acid sequence which encodes a chimeric TNF receptor (TNFR) which comprises (a) a binding domain which is capable of binding a TNFR ligand; and (b) a TNFR activating signalling domain.

Suitably, the chimeric TNF receptor (TNFR) which comprises (a) a binding domain which is capable of binding a TNFR ligand; and (b) a TNFR activating signalling domain may be encoded on a single nucleic acid sequence.

The present invention further provides a kit comprising nucleic acid sequences according to the present invention. For example, the kit may comprise (i) a first nucleic acid sequence which encodes i) a chimeric antigen receptor (CAR) or a transgenic T-cell receptor (TCR); and (ii) a second nucleic acid sequence which encodes a chimeric TNF receptor (TNFR) which comprises (a) a binding domain which is capable of binding a TNFR ligand; and (b) a TNFR activating signalling domain according to the present invention.

As used herein, the terms "polynucleotide", "nucleotide", and "nucleic acid" are intended to be synonymous with each other.

Suitably, the nucleic acid construct may comprise a plurality of nucleic acid sequences which encode different chimeric TNFRs as provided by the present invention. For example, the nucleic acid construct may comprise two, three, four or five nucleic acid sequences which different chimeric TNFRs of the invention. Suitably, the plurality of nucleic acid sequences may be separated by co-expression sites as defined herein.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described herein to reflect the codon usage of any particular host organism in which the polypeptides are to be expressed. Suitably, the polynucleotides of the present invention are codon optimised to enable expression in a mammalian cell, in particular an immune effector cell as described herein.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Co-Expression Site

A co-expression site is used herein to refer to a nucleic acid sequence enabling co-expression of both i) a chimeric antigen receptor (CAR) or a transgenic T-cell receptor (TCR); and (ii) a chimeric TNF receptor (TNFR) which comprises (a) a binding domain which is capable of binding a TNFR ligand; and (b) a TNFR activating signalling domain as defined herein.

The co-expression site may be a sequence encoding a cleavage site, such that the engineered polynucleotide encodes the enzymes of the transgenic synthetic biology pathway joined by a cleavage site(s). Typically, a co-expression site is located between adjacent polynucleotide sequences which encode separate enzymes of the transgenic synthetic biology pathway.

Suitably, in embodiments where a plurality of co-expression sites is present in the engineered polynucleotide, the same co-expression site may be used.

Preferably, the co-expression site is a cleavage site. The cleavage site may be any sequence which enables the two polypeptides to become separated. The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site. Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide. A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within Trypanosoma spp and a bacterial sequence (Donnelly et al., 2001) as above.

The co-expression sequence may be an internal ribosome entry sequence (IRES). The co-expressing sequence may be an internal promoter.

Vector

The present invention also provides a vector, or kit of vectors which comprises one or more nucleic acid sequence(s) or nucleic acid construct(s) of the invention. Such a vector may be used to introduce the nucleic acid sequence(s) or construct(s) into a host cell so that it expresses a CAR or transgenic TCR and a chimeric TNF receptor (TNFR) which comprises (a) a binding domain which is capable of binding a TNFR ligand; and (b) a TNFR activating signalling domain.

Suitably, the vector may comprise a plurality of nucleic acid sequences which encode different chimeric TNFRs as provided by the present invention. For example, the vector may comprise two, three, four or five nucleic acid sequences which different chimeric TNFRs of the invention. Suitably, the plurality of nucleic acid sequences may be separated by co-expression sites as defined herein.

The vector may, for example, be a plasmid or a viral vector, such as a retroviral vector or a lentiviral vector, or a transposon based vector or synthetic mRNA.

The vector may be capable of transfecting or transducing a cell.

Pharmaceutical Composition

The present invention also relates to a pharmaceutical composition containing a cell, a nucleic acid construct, a first nucleic acid sequence and a second nucleic acid sequence; a vector or a first and a second vector of the present invention. In particular, the invention relates to a pharmaceutical composition containing a cell according to the present invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering a cell, a nucleic acid construct, a first nucleic acid sequence and a second nucleic acid sequence; a vector or a first and a second vector of the present invention (for example in a pharmaceutical composition as described above) to a subject.

Suitably, the present methods for treating and/or preventing a disease may comprise administering a cell of the invention (for example in a pharmaceutical composition as described above) to a subject.

A method for treating a disease relates to the therapeutic use of the cells of the present invention. In this respect, the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. In this respect, the cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a cell-containing sample;
(ii) transducing or transfecting such cells with a nucleic acid sequence or vector provided by the present invention;
(iii) administering the cells from (ii) to a subject.

The present invention provides a cell, a nucleic acid construct, a first nucleic acid sequence and a second nucleic acid sequence, a vector, or a first and a second vector of the present invention for use in treating and/or preventing a disease. In particular the present invention provides a cell of the present invention for use in treating and/or preventing a disease The invention also relates to the use of a cell, a nucleic acid construct, a first nucleic acid sequence and a second nucleic acid sequence, a vector, or a first and a second vector of the present invention of the present invention in the manufacture of a medicament for the treatment and/or prevention of a disease. In particular, the invention relates to the use of a cell in the manufacture of a medicament for the treatment and/or prevention of a disease The disease to be treated and/or prevented by the method of the present invention may be cancer.

The cancer may be such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The cell, in particular the CAR cell, of the present invention may be capable of killing target cells, such as cancer cells. The target cell may be recognisable by expression of a TAA, for example the expression of a TAA provided above in Table 1. The cancer may be a cancer listed in Table 1.

Method of Making a Cell

CAR or transgenic TCR-expressing cells of the present invention may be generated by introducing DNA or RNA coding for the CAR or TCR and a chimeric TNF receptor (TNFR) which comprises (a) a binding domain which is capable of binding a TNFR ligand; and (b) a TNFR activating signalling domain by one of many means including transduction with a viral vector, transfection with DNA or RNA.

The cell of the invention may be made by:
(i) isolation of a cell-containing sample from a subject or one of the other sources listed above; and
(ii) transduction or transfection of the cells with one or more a nucleic acid sequence(s) or nucleic acid construct as defined above in vitro or ex vivo.

The cells may then by purified, for example, selected on the basis of expression of the antigen-binding domain of the antigen-binding polypeptide.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1

In Vitro Testing of a CD27-4-1 BB Chimeric TNF Receptor

Primary human T-cells are transduced to express CD19 CAR T-cells and additionally engineered to co-express a CD27-4-1BB chimeric TNF receptor. CD19 CAR T-cells and CD19 CAR T-cells co-expressing CD27-4-1BB are co-cultured with Raji tumour cell lines. Autologous monocytes or dendritic cells which express CD70 are co-cultured with the CAR T-cells/Raji cells. Killing of target cells is determined by flow-cytometry by counting the numbers of surviving target cells. Proliferation, phenotype and of CAR T-cells is determined by flow cytometry.

Example 2

In Vivo Testing of a CD27-4-1 BB Chimeric TNF Receptor

Mice are engrafted with the syngeneic A20 murine lymphoma engineered cell line (engineered to express firefly luciferase) by tail-vein injection. After 10-14 days, the A20 cell line engrafts in the bone-marrow, spleen and lymph node tissues. Murine T-cells are transduced with an anti-(murine)-CD19 CAR or transduced with a bicistronic vector which co-expresses an anti-(murine)-CD19 CAR along with a (murine) CD27-4-1BB chimeric TNF receptor. Three cohorts of A20 burdened mice are given either no CAR T-cells, antiCD19 CAR T-cells or anti-CD19/CD27-4-1BB CAR T-cells. Progression of the A20 tumour is measured by serial bioluminescent imaging. At the end of the experiment, mice are sacrificed, and a necropsy performed. CAR T-cell engraftment is determined by flow-cytometry of blood, marrow, spleen and lymph node tissues. Remaining tumour burden is also determined by flow-cytometry in these tissues as well as immunohistochemistry of bone marrow.

Example 3

In Vivo Testing of a RANK-4-1BB Chimera

NSG mice receive a tail vein injection of a myeloma cell line (MM1s) engineered to express firefly luciferase. This cell line homes to the bone-marrow of mice and causes lytic bone-lesions. Primary human T-cells are transduced with either a BCMA specific CAR or a cassette which co-expresses the BCMA CAR along with RANK-4-1BB chimeric TNF receptor. After 12 days, mice either receive non-transduced T-cells, BCMA-CAR T-cells or BCMA-CAR/RANK-4-1BB chimera T-cells. Progress of the tumour is determined by serial bioluminescence imaging. Bone lytic lesions are also measured by micro CT. Animals are sacrificed at the end of the experiment. Disease burden is determined by flow-cytometry and immunohistochemistry of bone marrow. Bone lytic lesions can also be measured through histochemistry of bone marrow. T-cell engraftment and persistence are determined by flow cytometry of marrow, spleen, blood and lymphnodes.

Example 4

In Vitro Testing of a fn14-4-1BB Chimera

Primary human T-cells are transduced with an EGFRvIII CAR or with a bicistronic vector co-expressing the EGFRvIII CAR and fn14-4-1BB chimeric TNF receptor. Co-cultures with either non-transduced T-cells, CAR T-cells or CAR/fn14-4-1BB T-cells are performed to include a human glioma cell line (such as A172 cell line, the LN-18 cell line or the Ln-229 cell line) engineered to express EGFRvIII. Parallel co-cultures are also performed identically but with the addition of stromal cells which secrete TWEAK. Killing of target cells and proliferation/differentiation of T-cells is determined by flow cytometry.

Example 5

In Vivo Testing of a fn14-4-1BB Chimera

Mice are orthotopically engrafted with the murine glioma cell line GL261 expressing murine EGFRvIII using stereotactic injection. Tumour engraftment and progression are determined and measured using micro MRI. Syngeneic splenocytes are transduced with EGFRvIII CAR or a bicistronic vector which co-expresses an EGFRvIII CAR and fn14-4-1BB chimeric TNF receptor. The splenocytes are additionally transduced to express firefly luciferase. GL261 bearing mice are irradiated with low dose (5Gy) total body irradiation and split into three cohorts: No CAR T-cells, EGFRvIII CAR T-cells and EGFRvIII/fn14-4-1BB CAR T-cells. T-cell trafficking, expansion and proliferation is determined through the experiment by serial biolumines-cence imaging. Tumour response is determined using micro MRI. At the end of the experiment, the mice are sacrificed. T-cell engraftment systemically is determined by flow-cytometry of bone-marrow, blood, spleen and lymph nodes. Mouse brains are harvested. Half are fixed, and tumour response/T-cell infiltration determined by immunohisto-chemistry. The other mouse brains are homogenized, and T-cells isolated using Percoll. Isolated T-cell number and quality is determined by flow-cytometry.

Example 6

In Vitro Testing of RANK-4-1 BB or HVEM-4-1BB chimeric TNF Receptor

Primary human T-cells were transduced to express a first-generation GD2 CAR alone or to co-express GD2 CAR with either a RANK-4-1BB or HVEM-4-1BB chimeric TNF receptor. CAR-T cells were co-cultured with target cells which either expressed the specific tumour antigen (Target cells) or not (Non target cells) in the presence or absence of cells presenting a ligand for the chimeric TNF receptor. Target cell killing was determined by flow-cytometry by counting the numbers of surviving target cells. Proliferation of CAR T-cells was also determined by flow cytometry.

Figure 4A:
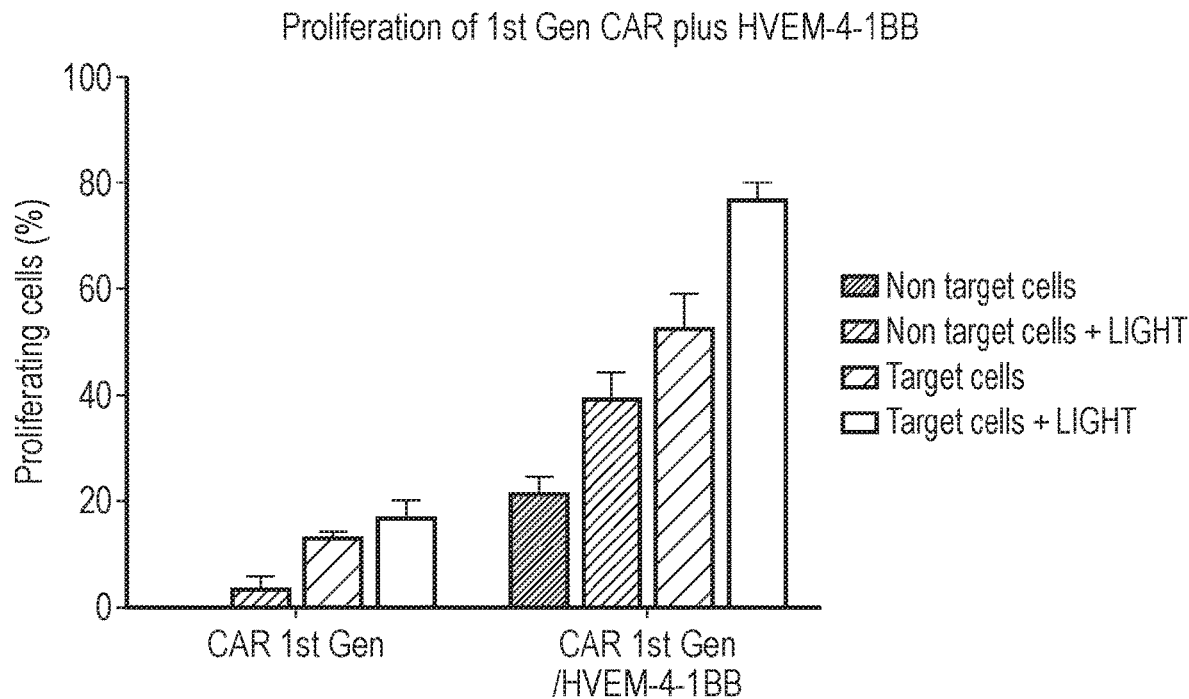
FIG. 4—Comparing the activity of cells expressing a GD2 CAR, with and without co-expression of a HVEM-4-1BB chimeric TNF receptor, in the presence or absence of cells presenting the ligand LIGHT, and in the presence of cells expressing the target antigen or not expressing the target antigen: a) proliferation; b) cytotoxicity against target cells.
Figure 4B:
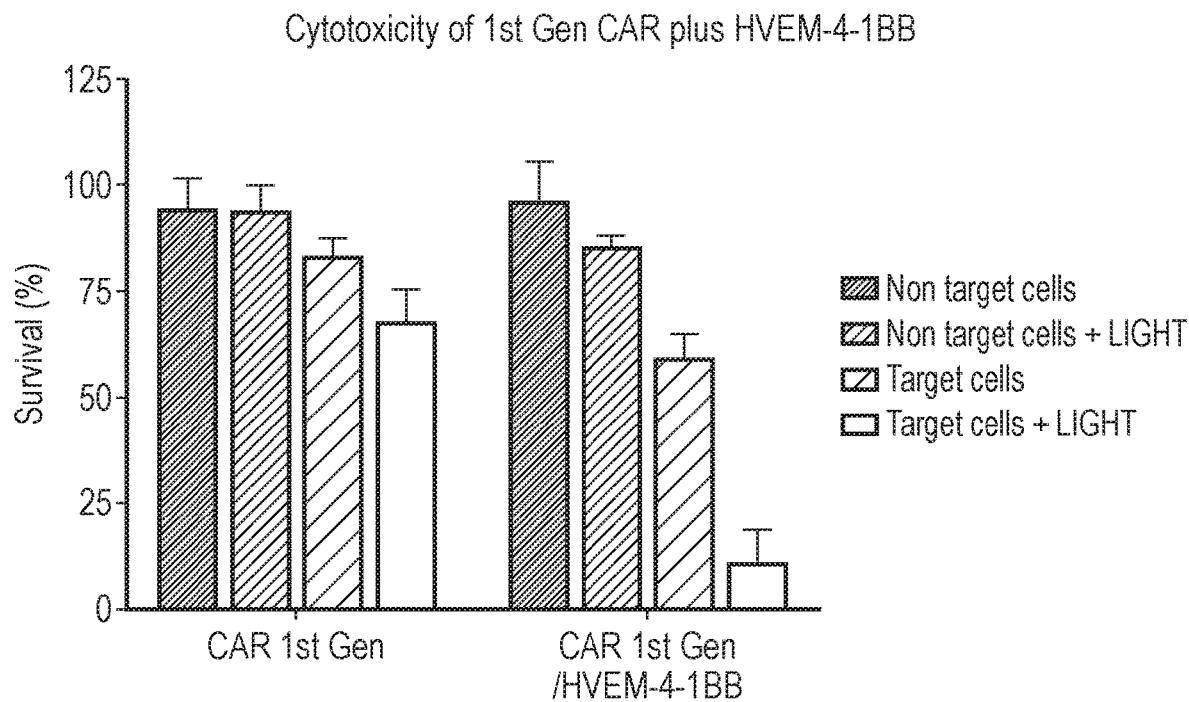
Figure 5A:
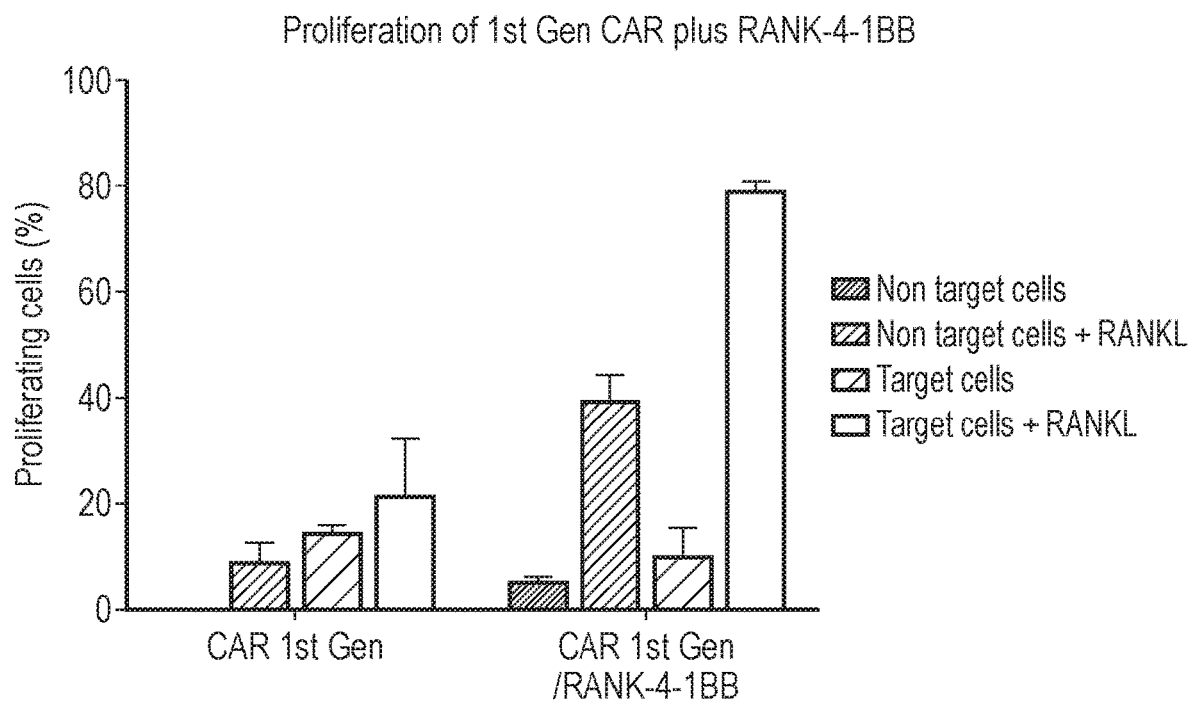
FIG. 5—Comparing the activity of cells expressing a GD2 CAR, with and without co-expression of a RANK-4-1BB chimeric TNF receptor, in the presence or absence of cells presenting the ligand RANKL, and in the presence of cells expressing the target antigen or not expressing the target antigen: a) proliferation; b) cytotoxicity against target cells.
Figure 5B:
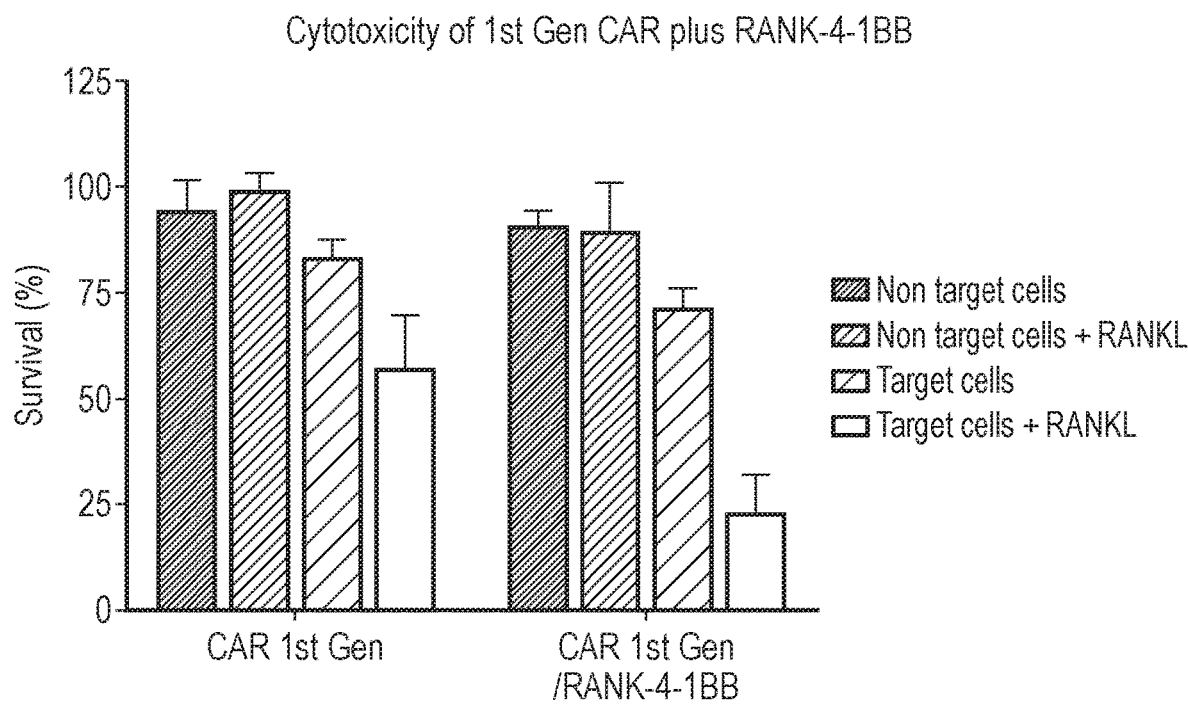

The results are shown in FIGS. 4 and 5. For both the HVEM-4-1BB chimeric TNF receptor (FIG. 4A) and the RANK-4-1BB chimeric TNF receptor (FIG. 5A), expression of the chimeric TNF receptor increased proliferation of T cells, especially in the presence of cells presenting a ligand for the TNF receptor. Expression of the chimeric TNF receptor also increased CAR-mediated target cell killing (FIGS. 4B and 5B) again especially in the presence of cells presenting a ligand for the TNF receptor.

Cell Culture and Reagents

All cell lines and primary T cells used in the experiments were cultured in RPMI 1640 medium (Lonza) supplemented with 10% fetal bovine serum (FBS, Biosera) and 1% L-Glutamine (GlutaMAX, Gibco). SupT1 cells were purchased from the ATCC. T cells were generated from PBMCs obtained from National Health Service Blood and Transplant (NHSBT; Colindale, UK). Transduced T cells were cultured in the same medium as stated before, with further addition of interleukin-2 (IL-2) at 100 U/mL.

Retro Viral and Plasmid Constructs

Molecular cloning was performed using a mixture of de novo gene synthesis of codon-optimized sequences using overlapping oligonucleotides and cloned into the CAR backbone. Each open reading frame was cloned into the SFG retroviral transfer vector. The TNF-4-1BB sequence was co-expressed by in-frame cloning of the foot- and mouth 2A self-cleaving peptide-based (2A peptide) multi-gene expression system. The RQR8 marker gene was also used, as described in WO2013/153391. RQR8 is recognized by the QBEND/10 anti-CD34 mAb. These markers were introduced into constructs with a codon wobbled 2A peptide in the configuration RQR8_CAR_TNF-4-1BB.

Transduction

The retrovirus was produced by transient transfection of 293T cells using GeneJuice (Millipore), with a plasmid encoding for gag-pol (pEQ-Pam3-E36), a plasmid encoding for the RD114 envelope (RDF37), and the desired retroviral transfer vector plasmid. Transduction was performed using Retronectin (Takara) as described previously. The transduction efficiency for the different constructs was assessed by flow cytometry based on the expression of RQR8 staining, performed using the QBEND/10 mAb. Flow cytometry analysis was performed using the MACSQuant Analyzer 10 (Miltenyi). Flow sorting was performed using a BD FACS.

T Cell Proliferation Assay

Cell Trace Violet (CTV) staining was carried out to assess the proliferation of T cells expressing the CAR and the CTNFR sequence (or CAR only) in co-cultures with target cells SupT1-GD2 (or SupT1-NT cells as control), in presence of TNF ligand presenting cells ("RANKL" or "LIGHT", as found in the figure). T cells expressing the different CAR constructs (NT T cells used as controls) were labelled with CTV before setup of co-cultures with target cells. Staining was performed by re-suspending the T cells at in fresh PBS containing CTV dye, according to the manufacturer's instructions. Co-cultures were at effector:target (E:T) cell ratio of 1:2. Proliferation was assessed by flow cytometry 5 days later. Cells were stained with 7-AAD and CD3 for exclusion of dead cells and detection of T cells, respectively. CTV-stained cells were used to measure proliferation by the extent of dye dilution of dead cells.

In Vitro Cytotoxicity Assays

T cells expressing the CAR and the TNF-4-1BB proteins (or CAR only) were depleted of CD56-expressing natural killers cells using the EasySep human CD56 positive selection kit (STEMCELL Technologies) according to the manufacturer's instructions. Cells were then used in cytotoxicity assays after 5 and 7 days. Cytotoxicity assays were set up at a 1:2 effector:target (E:T) cell ratio using SupT1 expressing the target in presence/absence of TNF ligand presenting cells ("RANKL" or "LIGHT", as found in the figure). SupT1 WT cells were used in the same conditions as control. Non transduced (NT) T cells were used in co-cultures with targets as a negative control. CAR-mediated cytotoxicity was assessed by flow cytometry after 5 days. T cells were identified from target cells by CD3 and staining. 7-AAD viability dye was used for exclusion of dead cells. Viable target cells were enumerated for each co-culture condition. The percentage of remaining target cells was calculated by normalizing the number of viable target cells of each condition to that recovered from co-cultures carried out with NT T cells (100%).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A cell which comprises:

(i) a chimeric antigen receptor (CAR) or a transgenic T-cell receptor (TCR); and (ii) a chimeric TNF receptor (TNFR) which comprises (a) a binding domain comprising the amino acid sequence of SEQ ID NO: 8 which is capable of binding a TNFR ligand of a first TNFR, wherein the first TNFR is RANK; and (b) a TNFR signalling domain of a second TNFR comprising an amino acid sequence of SEQ ID NO: 12, 13, 14, 15, 16 or 17.

2. A pharmaceutical composition which comprises a plurality of cells according to claim 1.

3. A method for making a cell according to claim 1, which comprises the step of introducing:

(i) a first nucleic acid sequence which encodes a chimeric antigen receptor (CAR) or a transgenic T-cell receptor (TCR); and (ii) a second nucleic acid sequence which encodes a chimeric TNF receptor (TNFR) which comprises (a) a binding domain comprising the amino acid sequence of SEQ ID NO: 8 which is capable of binding a TNFR ligand of a first TNFR, wherein the first TNFR is RANK; and (b) a TNFR signalling domain of a second TNFR comprising an amino acid sequence of SEQ ID NO: 12, 13, 14, 15, 16 or 17.

* * * * *